United States Patent
Luo

(10) Patent No.: US 10,463,568 B2
(45) Date of Patent: Nov. 5, 2019

(54) MOXA STICK, MOXIBUSTION DEVICE AND PREPARATION METHOD THEREOF

(71) Applicant: Shifu Luo, Beijing (CN)

(72) Inventor: Shifu Luo, Beijing (CN)

( * ) Notice: Subject to any disclaimer, the term of this patent is extended or adjusted under 35 U.S.C. 154(b) by 0 days.

(21) Appl. No.: 16/064,602

(22) PCT Filed: Dec. 19, 2016

(86) PCT No.: PCT/CN2016/110673
§ 371 (c)(1),
(2) Date: Nov. 6, 2018

(87) PCT Pub. No.: WO2017/107878
PCT Pub. Date: Jun. 29, 2017

(65) Prior Publication Data
US 2019/0060165 A1    Feb. 28, 2019

(30) Foreign Application Priority Data

Dec. 23, 2015 (CN) .......................... 2015 1 0969377

(51) Int. Cl.
| | | |
|---|---|---|
| A61K 36/00 | (2006.01) | |
| A61H 39/06 | (2006.01) | |
| A61K 47/44 | (2017.01) | |
| A61K 36/282 | (2006.01) | |
| A61K 36/185 | (2006.01) | |
| A61K 36/28 | (2006.01) | |
| A61K 36/30 | (2006.01) | |
| A61K 36/835 | (2006.01) | |
| A61K 36/9068 | (2006.01) | |

(52) U.S. Cl.
CPC .......... *A61H 39/06* (2013.01); *A61K 36/185* (2013.01); *A61K 36/28* (2013.01); *A61K 36/282* (2013.01); *A61K 36/30* (2013.01); *A61K 36/835* (2013.01); *A61K 36/9068* (2013.01); *A61K 47/44* (2013.01); *A61H 2201/0207* (2013.01); *A61H 2201/0278* (2013.01)

(58) Field of Classification Search
None
See application file for complete search history.

(56) References Cited

FOREIGN PATENT DOCUMENTS

| CN | 101112532 A | * | 1/2008 |
|---|---|---|---|
| CN | 101716212 A | | 6/2010 |
| CN | 103893545 A | | 7/2014 |
| CN | 104815072 A | | 8/2015 |
| CN | 105412938 A | | 3/2016 |
| JP | H09-077662 A | | 3/1997 |
| JP | 11-216169 A | | 10/1999 |
| JP | 11-347099 A | | 12/1999 |
| JP | 2014-064639 A | | 4/2014 |
| KR | 100839663 B1 | | 6/2008 |

OTHER PUBLICATIONS

1$^{st}$ Office Action issued in Chinese family member Patent Appl. No. 201510969377.2, dated Nov. 30, 2017, along with an English translation thereof.
2$^{nd}$ Office Action issued in Chinese family member Appl. No. 201510969377.2, dated Feb. 8, 2018, along with an English translation thereof.
Decision to Grant Patent issued Chinese family member Patent Application No. 201510969377.2, dated May 9, 2018, along with an English translation thereof.
International Search Report in WIPO Patent Application No. PCT/CN2016/110673, dated Mar. 22, 2017.

* cited by examiner

*Primary Examiner* — Qiuwen Mi
(74) *Attorney, Agent, or Firm* — Greenblum & Berenstein, P.L.C.

(57) ABSTRACT

A moxibustion device, comprising: a processed product of wormwood and oil and/or fat; the processed product of wormwood absorbs the oil and/or fat via contact, and was dried partially. The oil and/or fat are vegetable oil and/or fat, animal oil and/or fat, the processed products of vegetable oil and/or fat, or the processed products of animal oil and/or fat. The moxibustion device has better therapeutic effect than traditional moxibustion, with a favorable user experience and convenient use.

6 Claims, 3 Drawing Sheets

MOXA STICK, MOXIBUSTION DEVICE AND PREPARATION METHOD THEREOF

TECHNICAL FIELD

The present disclosure belongs to the field of medical equipment, specifically relates to the field of moxibustion equipment.

BACKGROUND

1. Scarring moxibustion. The main problems are as follows. (1) The pain during the process of giving moxibustion, the scar left after being given moxibustion, or the like is unacceptable. (2) Two or more acupoints may not be given moxibustion using only one moxa cone. If multiple acupoints are to be given moxibustion, multiple moxa cones have to be ignited at the same time. (3) There is a flame or a fire-point in the process of moxibustion treatment all the time, and it is easy to cause fire (for example, the conditioned reflex of limbs of people who receive moxibustion caused by the pain leads to the unexpected splash of the sparks of the moxa cones). (4) Moxibustion may not be given accurately to arbitrary acupoint all over the body, for example, moxibustion may hardly be given to positions such as armpit, perineum acupoint, and the like. (5) The smoke during burning is heavy, which pollutes the environment and causes physical harm as well.

2. Needle warming moxibustion. Needle warming moxibustion is an acupuncture manipulation that moxibustion is given at the needle handle when retaining the needle. The heat is introduced into body through the needle body when the mugwort floss is burning, exerts the synergistic effect of the needle and moxibustion, and is suitable for the diseases that need acupuncture and needle retaining as well as moxibustion. The existing problems are as follows. (1) The ash of Artemisiae Argyi Folium which is incompletely burned and still has sparks is easy to fall off in the burning process of the moxa cones, which burns the skin and causes unnecessary pain of people who receive moxibustion. (2) When moxibustion treatment is given, due to the limitation of the acupoints to which moxibustion is given, people who receive moxibustion are often required to lie flat on their backs or lie flat on their stomachs, therefore, it is also required that utensils such as beds or cushions are equipped during moxibustion, and it is also required that the operating space where moxibustion is given cannot be too narrow. (3) The smoke during burning is heavy. If moxibustion is not being dealt with appropriately, it is likely to seriously impair the respiratory system or the visual health of people who give moxibustion and people who receive moxibustion, and may it also cause different degrees of damage to the wall, furniture and the like in the house where moxibustion is given. (4) There is a flame or a fire-point in the process of moxibustion treatment all the time, and it is easy to cause fire (for example, the conditioned reflex of limbs of people who receive moxibustion caused by the pain leads to the unexpected splash of the sparks of the moxa cones). (5) It is required that the operator must be able to acupuncture the acupoints, and the difficulty of the operation is high.

3. Indirect moxibustion. Salt-partitioned moxibustion, ginger-partitioned moxibustion, garlic-partitioned moxibustion, green onion-partitioned moxibustion, medicinal cake-partitioned moxibustion, and the like are included. For example, the medicinal cake is set between the moxa cone and the acupoint, and the moxa cone is ignited and put on the medicinal cake to give moxibustion. The main problems are as follows. (1) The spacer needs to be thick, otherwise it is easy for the burning moxa cone to cause scald. However, the thickness may influence the distance between the moxa cone and the skin. Therefore, the therapeutic effect is limited. (2) The process of giving moxibustion relatively takes a long time, and people who receive moxibustion often need to keep a fixed pose for a long time, which is extremely easy to cause strain of muscle and tendon, thus leading to a situation of catching one and losing another. (3) The moxa cone set upon substances is not stable, and it is easy to cause unexpected accidents and even fire due to the shedding of the moxa cones. (4) Two or more acupoints may not be given moxibustion using only one moxa cone. If multiple acupoints are to be given moxibustion, multiple moxa cones have to be ignited at the same time. (5) When moxibustion treatment is given, due to the limitation of the acupoints to which moxibustion is given, people who receive moxibustion are often required to lie flat on their backs or lie flat on their stomachs, therefore it is required that utensils such as beds or cushions are equipped during moxibustion, and it is also required that the operating space where moxibustion is given cannot be too narrow.

4. Moxibustion by warming moxibustion apparatus. It is also referred to as warming moxibustion, which is actually one of the methods of medicated ironing. The existing problems are as follows. (1) The burning takes a long time, which produces a large amount of smoke, pollutes the environment and causes physical harm. (2) When using the warming moxibustion apparatus, strings are often needed to be used for fixation, thus it is easy to cause feeling of pressure to people who receive moxibustion, and even seriously hinder the blood circulation of the limbs of people who receive moxibustion. (3) Any warming moxibustion apparatus has a certain volume, if multiple sites need to be given moxibustion at the same time, it is required that multiple warming moxibustion apparatus are equipped, thus increasing the carrying burden of people who give moxibustion when they go out to give moxibustion.

5. Lamp moxibustion. When the lamp burns the skin of the acupoints, a slight "flap" sound may be heard, then the lamp is extinguished. This is referred to as one scorch. Generally, each acupoint is given moxibustion with only one scorch. There appears a slight blush locally after the moxibustion, and attention should be paid to cleaning to avoid infection. The existing problems are as follows. (1) There are many small burns at the fire of the moxibustion in this method and they are easy to be infected, as similar to the scarring moxibustion. (2) It is easy to drip during burning, which requires excellent techniques of the operators. (3) There is a flame or a fire-point in the process of moxibustion treatment all the time, and it is easy to cause fire (for example, the conditioned reflex of limbs of people who receive moxibustion caused by the pain leads to the unexpected splash of the sparks). (4) It is not convenient to use and carry.

6. Suspended moxibustion. The existing problems are as follows. (1) It stays a certain distance away from the skin. Although it is not easy to burn the skin, the distance may prevent the heat of the burning of moxa from going deep into the human body, the effect is greatly reduced, and this deficiency may be only compensated by prolonging the burning time (the duration of the moxibustion that aims at the acupoints of moxibustion should be sufficient, otherwise it is very difficult to achieve the expected effect). (2) The process of giving moxibustion takes too much time. If the people who give moxibustion give moxibustion by holding the moxa stick in hand, it will be labor intensive and very laborious, and with the decline of physical strength, it is extremely easy for people who give moxibustion give moxibustion to lose their concentration and burn the skin due to the unstable holding or the unconscious shake, thus causing unnecessary pain of people who receive moxibustion. It is also possible to deviate too far from the acupoints of moxibustion unconsciously so that the expected effect cannot be achieved. (3) For the ash of Artemisiae Argyi Folium which is incompletely burned and still has sparks, it is easy to fall off in the burning process of the moxa stick, burn the skin, and cause unnecessary pain of people who receive moxibustion. (4) People who receive moxibustion often need to keep a fixed pose for a long time, which may be extremely easy to cause the strain of muscle and tendon, thus leading to a situation of catching one and losing another.

7. Performing moxibustion by the above-mentioned traditional moxibustion methods utilizing the medicinal moxa stick. The existing problems are as follows. ① It is easy for drug powder to be mixed unevenly, which influences the exertion of the drug effects. ② An excessive amount of materials other than moxa is harmful to human body. Since moxibustion mainly takes advantage of the burning characteristics of Artemisiae Argyi Folium to perform moxibustion treatment and the burning characteristics of other materials are quite different from that of Artemisiae Argyi Folium, adding too much other materials may influence the effect of moxibustion, which does not conform to the traditional experience. Although the addition may be controlled by the amount of the drugs which are in the form of solid powder, the operation steps of this method is complicated. ③ The drug ingredients may not be absorbed efficiently by human body, resulting in great waste.

8. The traditional moxibustion often needs to be operated with fire, which is the characteristic of moxibustion. Therefore, there is no motivation in this field to try to extinguish the moxa stick for use. Besides, if the fire is extinguished by water, it may cause sharp decrease of the temperature of the moxa stick, and the therapeutic effect may be greatly reduced; if physical manners such as blowing out are simply used, the moxa stick may smolder after the open fire is extinguished, which is easy to cause scald. Also, as for the dry moxa stick, it is very difficult to extinguish the smoldering charcoal fire. Therefore, in general, the moxa sticks are all ignited for use when performing moxibustion.

9. External application method. It is a method in which the drug is ground into fine powder, and a paste formulation is formulated using the fine power together with a variety of different liquids and applied to certain acupoints or the affected parts so as to treat diseases. Moxa is not burned during the application process of this method, therefore, this method does not belong to the category of moxibustion. The principle, application method and points for attention thereof are all different from those of moxibustion, so that they cannot be used in a mixed way. The existing problems are as follows. There is no need to ignite the wormwood during the application process, the temperature is low, and the therapeutic effect of wormwood cannot be completely exerted.

SUMMARY

In order to solve the above-mentioned technical problems that the therapeutic effect of traditional moxibustion is limited, the user experience is poor, and the operation is inconvenient, the present disclosure proposes to prepare a novel moxibustion device by enabling the moxa stick to absorb oil and/or fat and then be dried incompletely, and a cover for moxibustion is utilized to wrap the moxibustion device after ignition.

A preparation method for a moxa stick, comprising:
step 1: preparing a ready-made moxa stick or selecting a ready-made moxa stick;
step 2: bringing the ready-made moxa stick into contact with an oil and/or fat;
step 3: taking out the ready-made moxa stick processed in step 2 and drying the ready-made moxa stick partially to prepare a moxa stick containing the oil and/or fat ingredient;
the weight of said oil and/or fat accounts for 10% or more of the total weight of the moxa stick, said oil and/or fat is one or more of a vegetable oil and/or fat, an animal oil and/or fat, a processed product of vegetable oil and/or fat, and a processed product of animal oil and/or fat.

A preparation method for a moxa stick, comprising:
step 1: preparing a medicinal moxa stick or selecting a ready-made medicinal moxa stick;
step 2: bringing the medicinal moxa stick into contact with an oil and/or fat;
step 3: taking out the medicinal moxa stick processed in step 2, drying it partially, and preparing a medicinal moxa stick containing the oil and/or fat ingredient;
the weight of said oil and/or fat accounts for 10% or more of the total weight of the moxa stick, said oil and/or fat is one or more of a vegetable oil and/or fat, an animal oil and/or fat, a processed product of vegetable oil and/or fat, and a processed product of animal oil and/or fat.

A preparation method for moxa stick, comprising:
step 1: preparing a ready-made moxa stick or selecting a ready-made moxa stick;
step 2: enabling an oil and/or fat to contain a drug ingredient through the contact of a drug with the oil and/or fat;
step 3: bringing the oil and/or fat containing the above-mentioned drug ingredient into contact with the ready-made moxa stick;
step 4: taking out the moxa stick processed in step 3 and drying the moxa stick partially to prepare a moxa stick containing the oil and/or fat and the drug ingredients;
the weight of said oil and/or fat accounts for 10% or more of the total weight of the moxa stick, said oil and/or fat is one or more of a vegetable oil and/or fat, an animal oil and/or fat, a processed product of vegetable oil and/or fat, and a processed product of animal oil and/or fat.

A preparation method for a moxa stick, comprising:
step 1: preparing a ready-made moxa stick or selecting a ready-made moxa stick;
step 2: bringing a drug and the ready-made moxa stick into contact with an oil and/or fat simultaneously to enable the ready-made moxa stick to absorb a drug ingredient in the oil and/or fat;
step 3: taking out the moxa stick processed in step 2 and drying the moxa stick partially to prepare a moxa stick containing the oil and/or fat and the drug ingredient;
the weight of said oil and/or fat accounts for 10% or more of the total weight of the moxa stick, said oil and/or fat is one or more of a vegetable oil and/or fat, an animal oil and/or fat, a processed product of vegetable oil and/or fat, and a processed product of animal oil and/or fat.

A preparation method for a moxa stick, comprising:
step 1: enabling an oil and/or fat to contain a drug ingredient through contact of a drug with the oil and/or fat;
step 2: filtering the oil and/or fat processed in step 1 and removing drug residue;

step 3: bringing a processed product of wormwood into contact with the oil and/or fat processed in step 2;

step 4: taking out the processed product of wormwood processed in step 3 and drying the processed product of wormwood partially to prepare a processed product of wormwood containing the oil and/or fat and the drug ingredient;

step 5: wrapping the processed product of wormwood processed in step 4 partially or completely with a wrapper, and preparing a moxa stick containing the oil and/or fat and the drug ingredient;

the weight of said oil and/or fat accounts for 10% or more of the total weight of the moxa stick, said oil and/or fat is one or more of a vegetable oil and/or fat, an animal oil and/or fat, a processed product of vegetable oil and/or fat, and a processed product of animal oil and/or fat.

A preparation method for a moxa stick, comprising:

step 1: enabling an oil and/or fat to contain a drug ingredient through contact of a drug with the oil and/or fat;

step 2: filtering the oil and/or fat processed in step 1 and removing drug residue;

step 3: bringing a processed product of wormwood and a wrapper into contact with the oil and/or fat processed in step 2 respectively;

step 4: taking out the processed product of wormwood processed in step 3 and the wrapper and drying the processed product of wormwood and the wrapper partially to prepare a processed product of wormwood containing the oil and/or fat and the drug ingredient and a wrapper containing the oil and/or fat and the drug ingredient;

step 5: wrapping the processed product of wormwood processed in step 4 partially or completely with the wrapper processed in step 4, and preparing a moxa stick containing the oil and/or fat and the drug ingredient;

the weight of said oil and/or fat accounts for 10% or more of the total weight of the moxa stick, said oil and/or fat is one or more of a vegetable oil and/or fat, an animal oil and/or fat, a processed product of vegetable oil and/or fat, and a processed product of animal oil and/or fat.

Further, the steps of bringing the processed product of wormwood and the wrapper into sufficient contact with the oil and/or fat processed in step 2 respectively in said step 3 are performed at the same time or performed stepwise.

A preparation method for a moxa stick, comprising:

step 1: preparing a ready-made moxa stick or selecting a ready-made moxa stick;

step 2: bringing a drug solution into contact with the ready-made moxa stick;

step 3: drying the moxa stick processed in step 2;

step 4: bringing the moxa stick processed in step 3 into contact with an oil and/or fat;

step 5: taking out the moxa stick processed in step 4 and drying the moxa stick partially to prepare a moxa stick containing the oil and/or fat and the drug ingredient;

the weight of said oil and/or fat accounts for 10% or more of the total weight of the moxa stick, said oil and/or fat is one or more of a vegetable oil and/or fat, an animal oil and/or fat, a processed product of vegetable oil and/or fat, and a processed product of animal oil and/or fat.

Further, said drug solution is prepared by bringing a drug into contact with water or an organic solvent, or said drug solution is a liquid drug.

A preparation method for a moxa stick, comprising:

step 1: bringing a drug solution into contact with a processed product of wormwood to prepare a processed product of medicinal wormwood containing a drug ingredient;

step 2: the processed product of medicinal wormwood processed in step 1;

step 3: preparing the processed product of medicinal wormwood processed in step 2 into a medicinal moxa stick;

step 4: bringing the medicinal moxa stick processed in step 3 into contact with an oil and/or fat;

step 5: taking out the medicinal moxa stick processed in step 4 and drying the medicinal moxa stick partially to prepare a moxa stick containing the oil and/or fat and the drug ingredient.

the weight of said oil and/or fat accounts for 10% or more of the total weight of the moxa stick, said oil and/or fat is one or more of a vegetable oil and/or fat, an animal oil and/or fat, a processed product of vegetable oil and/or fat, and a processed product of animal oil and/or fat.

A preparation method for a medicinal moxa stick, comprising:

bringing an oil and/or fat into contact with a moxa stick, or a processed product of wormwood, or a processed product of wormwood and a wrapper;

adding a drug in any one or more manners of the following methods: (1) adding the drug to the moxa stick in a solid form; (2) adding the drug to the moxa stick in a form of drug solution; (3) adding the drug or a drug ingredient to the moxa stick by bringing the drug into contact with said oil and/or fat; and preparing a medicinal moxa stick;

the weight of said oil and/or fat accounts for 10% or more of the total weight of the moxa stick, said oil and/or fat is a vegetable oil and/or fat, an animal oil and/or fat, a processed product of vegetable oil and/or fat, or a processed product of animal oil and/or fat.

Further, the weight of said oil and/or fat accounts for 20% to 70% of the total weight of the moxa stick.

Further, said processed product of wormwood is mugwort floss, Blumea balsamifera powder, stockpiled Artemisiae Argyi Folium, a moxa stick, or a processed product mixed with other materials and a wormwood ingredient.

Further, said contact includes one or more of soaking, flushing, drip filling, fumigating, spraying, or contacting dispersedly after solidification.

Further, said drug is a Chinese medicinal material, a Chinese medicine decoction piece, a Chinese patent medicine, a chemical raw medicine, and various essential oils.

A medicinal moxa stick, comprising a processed product of wormwood, a drug, and an oil and/or fat; a processed product of wormwood absorbs said oil and/or fat via contact; the weight of said oil and/or fat accounts for 10% or more of the total weight of the medicinal moxa stick, said oil and/or fat is a vegetable oil and/or fat, an animal oil and/or fat, a processed product of vegetable oil and/or fat, or a processed product of animal oil and/or fat; the drug is added in any one or more manners of the following methods: (1) adding the drug to the moxa stick in a solid form; (2) adding the drug to the moxa stick in a form of drug solution; (3) adding the drug or a drug ingredient to the moxa stick by bringing the drug into contact with said oil and/or fat.

A moxa stick, comprising a processed product of wormwood and an oil and/or fat; the processed product of wormwood absorbs said oil and/or fat via contact; the weight of said oil and/or fat accounts for 10% or more of the total weight of the moxa stick, and said oil and/or fat is a vegetable oil and/or fat, an animal oil and/or fat, a processed product of vegetable oil and/or fat or a processed product of animal oil and/or fat.

A medicinal moxa stick, comprising a processed product of wormwood, a drug, and an oil and/or fat; the processed product of wormwood absorbs said oil and/or fat via contact; the weight of said oil and/or fat accounts for 10% or more of the total weight of the medicinal moxa stick, said oil and/or fat is a vegetable oil and/or fat, an animal oil and/or fat, a processed product of vegetable oil and/or fat, or a processed product of animal oil and/or fat; said drug is partially or completely dissolved in said oil and/or fat.

Further, the moxa stick is one prepared by wrapping the processed product of wormwood partially or completely with a wrapper, or one prepared by the processed product of wormwood via a viscous substance or extrusion by an external force.

Further, the above-mentioned oil and/or fat include one or more of tea oil, sunflower oil, sea buckthorn seed oil, olive oil, sesame oil, peanut oil, Litsea Cubeba oil, rapeseed oil, palm oil, soybean oil, tung oil, corn oil, castor oil, lard oil, badger oil, sheep oil, beef lard, refined oil, mixed oil, or blend oil, or is a reprocessed product of one or more of the above-mentioned oils.

Further, the weight of said oil and/or fat accounts for 20% to 70% of the total weight of the moxa stick.

Further, said processed product of wormwood is mugwort floss, Blumea balsamifera powder, stockpiled Artemisiae Argyi Folium, a moxa stick, or a processed product mixed with other materials and a wormwood ingredient.

Further, in a normal temperature environment, the moxa stick is in an incompletely dry state.

Further, said contact includes one or more of soaking, flushing, drip filling, fumigating, spraying, or contacting dispersedly after solidification.

Further, the moxa stick may be a cylinder, a prism, a platform, a cone, a cuboid, or a combined shape thereof.

Further, the above-mentioned wrapper is paper, or cloth, or other processed products of plant fiber.

A moxa stick which is prepared by the above-mentioned preparation method of the moxa stick.

A moxibustion device, which comprises a moxa stick and a cover for moxibustion; the moxa stick is the above-mentioned moxa stick; under an application state, the ignited moxa stick is partially or completely wrapped with said cover for moxibustion, said cover for moxibustion is used as a spacer between the moxa stick and the skin of human body.

Further, the material of the cover for moxibustion is paper, or cloth, or other processed products of plant fiber.

Further, at an opening of the cover for moxibustion, there is a control device used to control the size of the opening, and the control device may be one or more of a string, a rubber band, a clip or a metal ring.

Explanation and Description:

Said oil and/or fat do not include an oil and/or fat ingredient that are contained in the processed products of wormwood themselves, and do not appear in the form of an oil and/or fat in the natural state, but may be separated by means of distillation and the like. That is, said oil and/or fat of the present disclosure do not include the oil and/or fat naturally contained in wormwood itself, which is a kind of plant, but refer to an oil and/or fat added externally instead. When used in the claims and/or the specification, the word "a" or "an" or "the" may refer to "one", but may also refer to "one or more", "at least one" and "one or more than one."

Oil and/or fat is a generic name for fatty oils and fats. The oil and/or fat in nature is a mixture of a variety of substances, and its main ingredients are the glycerides of fatty acids. Under room temperature, it is referred to as lipids or fats if it is in a solid or semi-solid state, and is referred to as oils or fatty oils if it is in a liquid state. Examples are: a vegetable oil and/or fat such as tea oil, sunflower oil, olive oil, sesame oil, peanut oil, rapeseed oil, palm oil, soybean oil, tung oil, corn oil and castor oil; an animal oil and/or fat such as lard oil, badger oil, sheep oil and beef lard; a processed product of oil and/or fat such as refined oil, mixed oil and blend oil.

The processed products of wormwood may be mugwort floss, or Blumea balsamifera powder, or a processed product of wormwood mixed with other materials, as well as all other processed products containing wormwood ingredient. For example, mugwort floss is the most common processed product of wormwood, and refers to a velvet-like substance processed and prepared from Artemisiae Argyi Folium.

The portion which contains a wormwood ingredient in a moxibustion device is collectively referred to as "moxa stick", which is the key portion of the moxibustion device, or the moxa stick may also be the whole moxibustion device. The word "moxa stick" does not define its shape, although the commonly used moxa stick is strip-shaped. The moxa stick may be a cylinder, a prism, a platform, a cone, a cuboid, a cube, or a combined shape thereof, for example, it may also be a body with irregular shape. Meanwhile, this name defines neither its volume nor length, for example, the moxa stick may be a cylinder-shaped long moxa stick, or may also be a cylinder-shaped short moxa stick, and even a cylinder-shaped flake-like moxa stick, etc., and the same applies to other shapes. The moxa stick may be prepared by wrapping mugwort floss with paper, cloth, and the like. It is also possible that the moxa stick is prepared directly by mixing mugwort floss with a viscous substance without the need of wrapping, or the moxa stick is prepared by extruding mugwort floss with an external force. The moxa stick prepared by wrapping or viscous substance usually has a relatively fixed shape, while the shape of the moxa stick prepared by extruding the processed products of wormwood such as mugwort floss by an external force may be fixed or not fixed. For example, when extruding with a stronger external force to enable the mugwort floss to be tightly molded between each other and form the moxa stick, the shape of the mugwort floss substantially maintains unchanged after the force is removed; it is also possible to use a tiny force to enable the mugwort floss to gather together and form the moxa stick, and after the force is removed, the shape of the mugwort floss maintains unchanged, changes naturally, or changes under the effect of other external forces. The most common moxa stick includes cladding(s) and an inner core portion, the inner core portion is wrapped with the cladding(s). The cladding(s) may be a single layer or multiple layers. The material of the wrapper which forms the cladding(s) may be paper, including cotton paper, Chinese art paper, kraft paper, straw paper, as well as other paper suitable for preparing the moxa stick. Other materials suitable for preparing the moxa stick (such as cotton cloth and nonwoven fabric) may also be used for the cladding(s). The ordinary moxa stick may be the pure moxa stick containing no drug, and may also be the medicinal moxa stick containing drugs.

The ready-made moxa stick refers to the moxa stick which is processed using wormwood and is capable of being used to perform moxibustion.

The moxibustion device refers to a device which may be used for moxibustion directly and is an appliance used to perform moxibustion for treatment and healthcare. For example, in the present disclosure, the device prepared by igniting the moxa stick containing oil and/or fat, wrapping the moxa stick partially or completely with a cover for moxibustion, and extinguishing the open fire may be used to perform the operation of moxibustion directly without needing to perform other operations any more.

Drying partially means that the moxa stick or the processed product of wormwood is subjected to drying operation by adopting ways such as drying in shade (other ways of drying, such as spin-drying, drying in the air, etc., may also be adopted) after being brought into contact with the oil and/or fat, while the prepared moxa stick or the processed product of wormwood is ensured to maintain in a wet state which is incompletely dry.

"The weight of the oil and/or fat accounts for n % of the total weight of the moxa stick" means that the ratio of the weight of the oil and/or fat in the moxa stick prepared according to the method of the present disclosure to the total weight of the moxa stick (containing oil and/or fat, or containing oil and/or fat and a drug ingredient) prepared according to method of the present disclosure is n %. The above percentage is achieved by controlling the contacting time and/or the contacting manner with the oil and/or fat. When the ratio is calculated specifically, the moxa stick containing no oil and/or fat/the processed product of wormwood containing no oil and/or fat may be first weighed as weight A, then the moxa stick containing oil and/or fat/the processed product of wormwood containing oil and/or fat is weighed as weight B, and $(B-A)/B*100\%$ is used for calculation. However, in practical production, for the sake of convenience, by first weighing the moxa stick containing oils/the processed product of wormwood containing oils as weight A, then weighing the substance containing no oil and/or fat to obtain weight B or directly obtain the weight C of the oil and/or fat by separating the oil and/or fat in the moxa stick/the processed product of wormwood substantially via manners such as physical squeezing, heating, centrifugation and chemical extraction, the oil content n % may be obtained by calculating from $(A-B)/A*100\%$ or $C/A*100\%$. Meanwhile, if there is a portion which does not contain oil at all or contains oil unevenly in the moxa stick, then in the moxa stick containing oil and/or fat/the processed product of wormwood containing oil and/or fat, the percentage of the weight of the oil and/or fat of any portion L which contains the oil and/or fat to the total weight of the portion L may be referred to as the oil content (for example, the oil content being 40% means that even if the moxa stick/the processed product of wormwood contains oil and/or fat unevenly, there is at least a portion L. and the weight of the oil and/or fat in L portion accounts for 40% of the total weight of L portion). In the moxa stick containing oil and/or fat/the processed product of wormwood containing oil and/or fat, the percentage of the weight of the oil and/or fat of the portion L which contains the oil and/or fat and is able to exert therapeutic effect to the total weight of the portion L may also referred to as the oil content. Operations may also be similarly performed using the determination methods for the oil content of vegetable oils as reference, for example, GB/T10359-2008, GB/T14488.1-2008, NY/T1285-2007, GB/T3554-2008, and GB/T15690-2008. The above are only limited examples, and may also be obtained from other methods that may be conceived by those skilled in the art by tests and/or calculations. It is understood by those skilled in the art that any method capable of substantially removing oil and/or fat from an object may be used to judge the oil content. In the actual determination of the content of the oil and/or fat, it is not necessary to over-emphasize the "complete" removal/separation of oil and/or fat which is actually unachievable and only exists in theory.

Drugs refer to substances that are used to prevent, treat and diagnose human diseases, regulate the physiological function of human purposefully, and that have specified indications or major functions, methods of administration and dosages. Said drug include a Chinese medicinal material, a Chinese medicine decoction piece, a Chinese patent medicine, a chemical raw medicine, various essential oils, and the like. The drug(s) used during the preparation of the novel medicinal moxa stick may be a certain kind of drug, and may also be a combination of drugs formed by two or more drugs. "Drug is dissolved in an oil and/or fat" means that the drug is brought into contact with the oil and/or fat before or after the drug is added to the moxa stick, and the drug ingredients are partially or completely dissolved in the oil and/or fat.

When using the moxa stick prepared in the present disclosure, drug ingredients permeate with the oil and/or fat to contact with the skin and generate therapeutic effects, therefore, all drugs whose effective ingredients may be dissolved in liquids may be used in the present disclosure, and there is no need to limit the type of drugs. In the examples of the present disclosure, methods of manufacturing the moxa stick using a variety of drugs as well as methods of using the moxa stick are exemplified, however, it may be understood that those in examples are merely examples, and the remaining drugs may also be used in the present disclosure.

Effects of Disclosure

As compared with the traditional moxibustion methods, the present disclosure has better therapeutic and health care effect as well as better user experience.

Specifically, reference may be made to the technical effects described in detail in the specific embodiments. Taking certain examples as examples, the technical effects that may be achieved are for example as follows. (1) The moxa sticks in the examples contain oil(s) and/or fat(s), and are in an incompletely dry state. At the time of burning, the oil(s) and/or fat(s) in a liquid state contribute to extinguishing the fire instantly with dry paper or cloth, and the moxa sticks may be used in a flameless state, thus reducing the possibility of scald and fire disaster, making it possible for the moxa sticks to have a close contact with the skin, and being able to strengthen the therapeutic effect of moxibustion (the traditional moxibustion stays far away from the skin, therefore, the effect is limited). Besides, the smoke is reduced, which is more environmentally friendly and comfortable. Since the burning time of the open fire is very short, the materials of the moxa stick are saved and the service life is long. Moreover, there will be a small amount of oil(s) and/or fat(s) permeating out from the cover for moxibustion, and the effective ingredients of wormwood or the drug ingredient(s) dissolved in the oil(s) and/or fat(s) are able to be absorbed by the skin directly. Besides, the whole process is assisted by moxibustion for absorption, the therapeutic effect is more direct, and a new route for the drug(s) to be absorbed by human body is innovated. (2) If the moxibustion materials containing oil(s) and/or fat(s) are directly ignited and used without being dried, oil(s) may drip during the application process to cause danger and injury. In the examples, the moxa sticks containing oil(s) and/or fat(s) are partially dried and the oil dripping may be prevented. Therefore, it is safer, and there is no need to carry the oil(s) and/or fat(s) additionally, thus being more convenient to use (for example, it may pass through the security check at airports). (3) In the examples, by making the moxa stick, the oil(s) and/or fat(s) and the drug(s) contact with each other, the drug ingredient(s) is made to be dissolved in the oil(s) and/or fat(s), the method of adding the drug ingredients in the preparation process of the medicinal moxa stick is innovated, the addition is more convenient, the drug ingredient(s) are distributed evenly in the moxa stick, and the excessive impurities may also be avoided. (4) In the examples, after the moxa sticks have burned for a short period of time and are wrapped with dry paper or cloth to extinguish the fire, it is able to give moxibustion to multiple acupoints along a certain meridian continuously and conveniently by the residual heat (the traditional moxibustion may only be given to a fixed acupoint, and is not easy to move). In addition, there is no need of complicated devices, and moxibustion may be given to arbitrary acupoints all over the body accurately, especially the acupoints such as armpit which are traditionally inconvenient for moxibustion. (5) The cover for moxibustion is used for wrapping during the application process, which may effectively prevent the moxa stick from dropping ash, which may cause scald or contaminate the skin.

Figure 1:
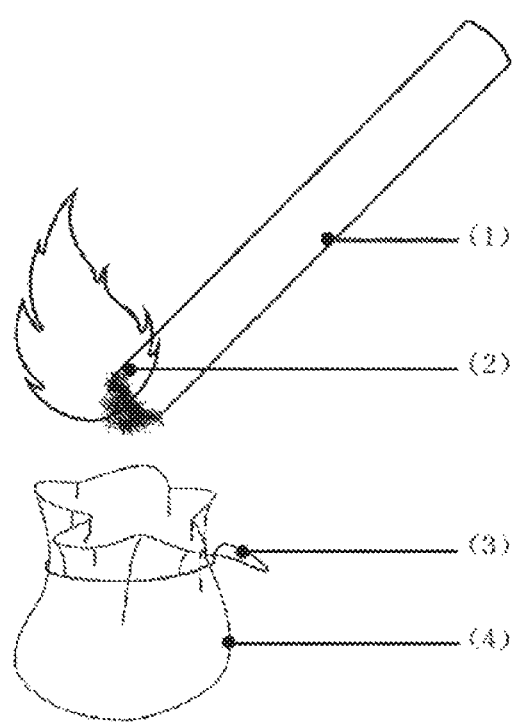
FIG. 1 is a schematic view of application step 1 of the present disclosure.
Figure 2:
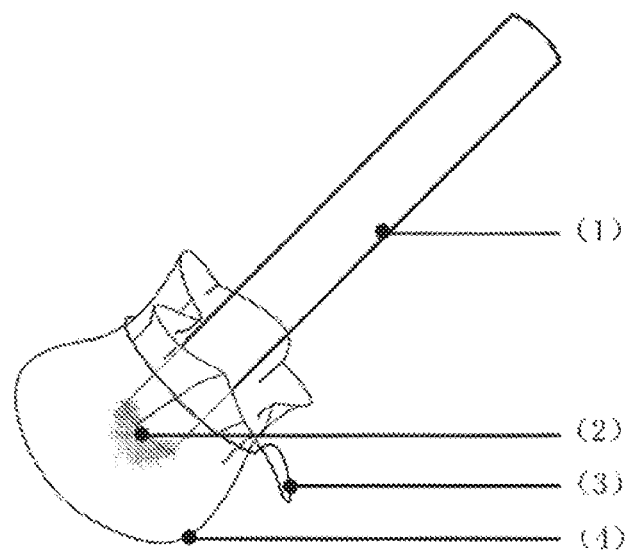
FIG. 2 is a schematic view of application step 2 of the present disclosure.
Figure 3:
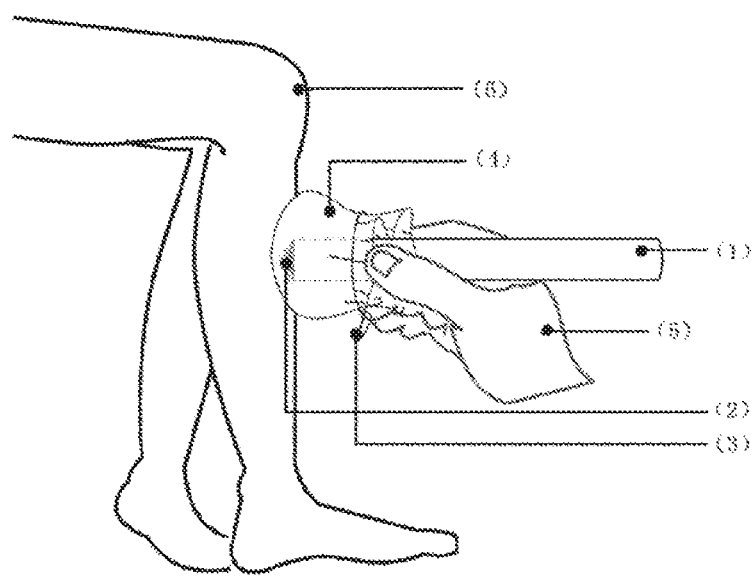
FIG. 3 is a schematic view of application step 3 of the present disclosure.

(1) is a moxa stick; (2) is a burning end; (3) is a string; (4) is a cover for moxibustion; (5) is the hand of a person who gives moxibustion; (6) is the body of a person who receives moxibustion.

DETAILED DESCRIPTION (1) A First Preparation Method for a Moxa Stick
Preparation Steps:
Step 1: A moxa stick was prepared or a ready-made moxa stick was selected. Mugwort floss was wrapped with cotton paper and the like to prepare a stripe. According to whether moxa stick contained drug(s), they were further divided into two types: ordinary pure moxa sticks and ordinary medicinal moxa sticks. The ordinary pure moxa sticks and the drug-containing ordinary medicinal moxa sticks all belonged to ordinary moxa sticks. For example, 24 gram of mugwort floss (or 6 to 8 gram of the drug powder such as Sophorae flavescentis radix and the like was added) was taken and tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form the ordinary pure moxa stick (or the ordinary medicinal moxa stick). According to the amount of the mugwort floss and the size of the cotton paper, ordinary moxa sticks of different sizes could be prepared. The ready-made moxa stick could also be bought directly from the market.

Step 2: The moxa stick was brought into sufficient contact with an oil and/or fat. The moxa stick was brought into sufficient contact (the contacting manners included but were not limited to soaking, circulating flushing, and the like) with an oil and/or fat (in usual cases, contacting for 1 hour or more was generally recommended), enabling the moxa stick to absorb the oil and/or fat sufficiently. According to experiments, the contacting time was preferably 5 hours or more. Said oil and/or fat was a vegetable oil and/or fat, a animal oil and/or fat, a processed product of vegetable oil and/or fat or a processed product of animal oil and/or fat, for example, tea oil and the like.

Step 3: The moxa stick processed in Step 2 was taken out and dried partially to prepare a moxa stick containing oil and/or fat. In the prepared moxa stick containing oil and/or fat, the weight of the oil and/or fat accounted for 10% or more, more preferably 20% to 70%, most preferably 30% to 60% of the total weight. This standard was suitable for various preparation methods described as follows, and a redundant description would not be provided.

Unique advantages: (1) Since Step 2 was adopted, the oil and/or fat contained in the prepared moxa stick was 10% or more, which was in an incompletely dry state, dry paper or cloth could be used to extinguish the fire instantly at the time of burning. As compared with ordinary moxa sticks, the problems that the moxa stick was burning all the time during the application process and caused large amount of smoke were solved, and the effects of generating less smoke as well as saving energy and protecting the environment were achieved. (2) Since Step 2 was adopted, the oil and/or fat contained in the prepared moxa stick was 10% or more, and the moxa stick was in an incompletely dry state, so that dry paper or cloth could be used to extinguish the fire instantly when burning. As compared with the ordinary moxa stick, the problems that the moxa stick was burning all the time during the application process and it was easy to cause scald were solved, and the effect of using with more safety was achieved. (3) Since Step 2 was adopted, the oil and/or fat contained in the prepared moxa stick was 10% or more, and the moxa stick was in an incompletely dry state. This enabled the fire to be mild at the time of burning, and hot and dry charcoal fire generated when the dry moxa stick was burning would not be produced, and a small amount of oil and/or fat permeated after the moxa stick was wrapped with dry paper or cloth. As compared with the ordinary dry moxa stick, the problem that the hot and dry charcoal fire generated when the dry moxa stick was burning caused the dry skin of the people who received moxibustion was solved, and the effect of being more beneficial to human health was achieved.

(2) A Second Preparation Method for a Moxa Stick
Preparation Steps:
Step 1: A medicinal moxa stick was prepared or a ready-made medicinal moxa stick was selected. Cotton paper or the like was used to wrap the mugwort floss containing drug (for example, Coptidis rhizoma, etc.) powder to prepare a stripe. The moxa stick herein contained drug powder and was a medicinal moxa stick. For example, 24 gram of mugwort floss was taken, 6 to 8 gram of the drug powder was added, and the mugwort floss and the drug powder were tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form the medicinal moxa stick. According to the amount of the mugwort floss and the size of the cotton paper, medicinal moxa sticks of different sizes could be prepared. The ready-made medicinal moxa stick could also be bought directly from the market.

Step 2: The medicinal moxa stick was brought into sufficient contact with oil and/or fat. The medicinal moxa stick was brought into sufficient contact (the contacting manners included but were not limited to soaking, circulating flushing, and the like) with the oil and/or fat (in usual cases, contacting for 1 hour or more was generally recommended), enabling the medicinal moxa stick to absorb the oil and/or fat sufficiently. According to experiments, the contacting time was preferably 5 hours or more. Said oil and/or fat was a vegetable oil and/or fat, an animal oil and/or fat, a processed product of vegetable oil and/or fat or a processed product of animal oil and/or fat, for example, sesame oil, etc.

Step 3: The medicinal moxa stick processed in step 2 was taken out and dried partially to prepare a medicinal moxa stick containing 10% or more of the oil and/or fat, in particular, a medicinal moxa stick containing 50% of the oil and/or fat could be prepared.

Unique advantages: similar to the above-mentioned advantages.

(3) A Third Preparation Method for a Moxa Stick
Preparation Steps:

Step 1: A moxa stick was prepared or a ready-made moxa stick was selected. Mugwort floss was wrapped with cotton paper and the like to prepare a stripe. According to whether moxa sticks contained drug(s), they were further divided into two types: ordinary pure moxa sticks and ordinary medicinal moxa sticks. The ordinary pure moxa sticks and the drug-containing ordinary medicinal moxa sticks all belonged to ordinary moxa sticks. For example, 24 gram of mugwort floss was taken (or 6 to 8 gram of the drug powder such as Ephedrae herba, Cinnamomi ramulus, Perilla frutescens, Zingiberis rhizoma recens, and the like was added) and tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form an ordinary pure moxa stick (or an ordinary medicinal moxa stick). According to the amount of the mugwort floss and the size of the cotton paper, ordinary moxa sticks of different sizes could be prepared. The ready-made moxa stick could also be bought directly from the market.

Step 2: Oil and/or fat were made to contain drug ingredient(s) by bringing the drug(s) into contact with the oil and/or fat sufficiently. The drug(s) were soaked with the oil and/or fat (for example, sesame oil, etc.) sufficiently (in usual cases, 1 hour or more was generally recommended), enabling the drug ingredient(s) to be fully blended in the oil and/or fat. According to experiments, the soaking time was different for different drugs, for example, the soaking time of drugs easily soluble in oil and/or fat was short; otherwise the soaking time was long.

Step 3: The moxa stick was brought into sufficient contact with the oil and/or fat containing the above-mentioned drug ingredient(s), enabling the moxa stick to absorb the drug ingredient(s) dissolved in the oil and/or fat sufficiently. The ordinary moxa stick was brought into sufficient contact (the contacting manners included but were not limited to soaking, circulating flushing, and the like) with the oil and/or fat containing the drug ingredient(s) (in usual cases, contacting for 1 hour or more was generally recommended), enabling the ordinary moxa stick to sufficiently absorb the oil and/or fat containing the drug ingredient(s). According to experiments, the contacting time was preferably 5 hours or more.

Step 4: The moxa stick processed in step 3 was taken out and dried partially to prepare a moxa stick containing the oil and/or fat and the drug ingredient(s). The soaking time was controlled to prepare a medicinal moxa stick containing 60% of the oil and/or fat.

Unique advantages: (1) Since Step 2 and Step 3 were adopted, the effective drug ingredient(s) could be added without adding the drug powder. As compared with the ordinary medicinal moxa sticks (for example, thunder-fire miraculous moxa stick and taiyi miraculous moxa stick), the problem that drug(s) could only be added by mixing the drug powder was solved, and the effect of completely changing the route of adding drug(s) was achieved. (2) Since Step 2 and Step 3 were adopted, there was no need to first grind the drug(s) into powder (or use a grinding machine to produce powder) and the drug(s) were soaked directly instead. As compared with the ordinary medicinal moxa sticks (for example, thunder-fire miraculous moxa stick and taiyi miraculous moxa stick), the problem that a grinding apparatus was needed was solved, and the effect of simplifying the preparation process was achieved. (3) Since Step 2 and Step 3 were adopted, as compared with the ordinary medicinal moxa sticks (for example, thunder-fire miraculous moxa stick and taiyi miraculous moxa stick), the problem that the drug powder might not be distributed evenly was solved, and the effect of the uniform distribution of the drug ingredient(s) was achieved. (4) Since Step 2 and Step 3 were adopted, the moxa stick was soaked with the oil and/or fat containing the drug ingredient(s). As compared with the ordinary medicinal moxa sticks (for example, thunder-fire miraculous moxa stick and taiyi miraculous moxa stick), the problem that the content of the drug powder might be too high was solved, and the effect of not increasing the powdery solid ingredient(s) was achieved. (5) Other effects were similar to those of the above-mentioned methods.

(4) A Forth Preparation Method for a Moxa Stick:
Preparation Steps:

Step 1: A moxa stick was prepared or a ready-made moxa stick was selected; mugwort floss was wrapped with cotton paper and the like to prepare a stripe. According to whether moxa sticks contained drug(s), they were further divided into two types: ordinary pure moxa sticks and ordinary medicinal moxa sticks. The ordinary pure moxa sticks and the drug-containing ordinary medicinal moxa sticks all belonged to ordinary moxa sticks. For example, 24 gram of mugwort floss was taken (or 6 to 8 gram of the drug powder such as Lonicerae japonicae flos, Forsythiae fructus, Andrographis herba, Isatidis folium and the like was added) and tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form an ordinary pure moxa stick (or an ordinary medicinal moxa stick). According to the amount of the mugwort floss and the size of the cotton paper, ordinary moxa sticks of different sizes could be prepared. The ready-made moxa stick could also be bought directly from the market.

Step 2: The drug(s) and the moxa stick were brought into contact with an oil and/or fat (for example, sunflower seed oil) at the same time, enabling the moxa stick to absorb the drug ingredient(s) dissolved in the oil and/or fat sufficiently. The ordinary moxa stick and the drug(s) were brought into contact with the oil and/or fat sufficiently at the same time (the contacting manners included but were not limited to soaking, circulating flushing, and the like. In usual cases, contacting for 1 hour or more was recommended). According to experiments, the contacting time was different for different drugs, for example, the contacting time of drug(s) easily soluble in oil and/or fat was short; otherwise the contacting time was long. According to experiments, the contacting time was preferably 5 hours or more.

Step 3: The moxa stick processed in Step 2 was taken out and dried partially to prepare a moxa stick containing the oil and/or fat and the drug ingredient(s). The content of the oil and/or fat was 10% or more, in particular, 70%.

Unique advantages: similar to the above-mentioned forth preparation method.

(5) A Fifth Preparation Method for a Medicinal Moxa Stick

Preparation Steps:

Step 1: Contain drug ingredient(s) in an oil and/or fat by bringing a drug(s) (for example, Aconiti Radix, Agkistrodon, Zaocys, Chaenomelis Fructus, silkworm excrement, etc.) into contact with the oil and/or fat sufficiently. The drug(s) were brought into sufficient contact (the contacting manners included but were not limited to soaking, circulating flushing, and the like) with the oil and/or fat (for example, a mixed oil of peanut oil and sesame oil, or edible blend oils were used directly) (in usual cases, contacting for 1 hour or more was generally recommended), enabling the drug ingredient(s) to be fully blended in the oil and/or fat. According to experiments, the contacting time was different for different drugs, for example, the contacting time of drugs easily soluble in oil and/or fat was short; otherwise the contacting time was long.

Step 2: The oil and/or fat processed in Step 1 were filtered, and the drug residue was removed.

Step 3: Mugwort floss was brought into sufficient contact with the oil and/or fat processed in Step 2. The oil and/or fat containing the drug ingredient(s) were filtered to remove the drug residue in Step 1, then ordinary mugwort floss was brought into sufficient contact with the filtered oil and/or fat (the contacting manners included but were not limited to soaking, circulating flushing, and the like. In usual cases, contacting for 1 hour or more was generally recommended), enabling the ordinary mugwort floss to sufficiently absorb the vegetable oils containing the drug ingredient(s). According to experiments, the contacting time was preferably 5 hours or more.

Step 4: The mugwort floss processed in Step 3 was taken out and dried partially to prepare the mugwort floss containing the oil and/or fat and the drug ingredient(s).

Step 5: The mugwort floss processed in Step 4 was wrapped with a wrapper to prepare a moxa stick containing the oil and/or fat and the drug ingredient(s). The content of the oil and/or fat was 10% or more, for example, 30%.

Unique advantages: similar to the above-mentioned effects.

(6) A Sixth Preparation Method for a Moxa Stick

Preparation Steps:

Step 1: Drug ingredient(s) was contained in an oil and/or fat by bringing the drug(s) into contact with the oil and/or fat (for example, plant essential oils) sufficiently. The drug(s) was brought into sufficient contact (the contacting manners included but were not limited to soaking, circulating flushing, and the like) with the oil and/or fat (in usual cases, contacting for 1 hour or more was generally recommended), enabling the drug ingredient(s) to be fully blended in the oil and/or fat. According to experiments, the contacting time was different for different drugs, for example, the contacting time of drugs easily soluble in oil and/or fat was short: otherwise the contacting time was long.

Step 2: The oil and/or fat processed in Step 1 were filtered, and the drug residue was removed.

Step 3: Mugwort floss and wrapper were separately brought into sufficient contact with the oil and/or fat processed in Step 2. The mugwort floss and the wrapper were separately brought into sufficient contact with the oil and/or fat processed in Step 2 (the contacting manners included but were not limited to soaking, circulating flushing, and the like. In usual cases, contacting for 1 hour or more was generally recommended), enabling the mugwort floss and the wrapper to sufficiently absorb the vegetable oils containing the drug ingredient(s). According to experiments, the contacting time was preferably 5 hours or more.

Step 4: The mugwort floss processed in Step 3 was taken out and dried partially to prepare mugwort floss containing the oil and/or fat.

Step 5: The wrapper processed in Step 3 was taken out and dried partially to prepare a wrapper containing the oil and/or fat.

Step 6: The mugwort floss processed in Step 4 was wrapped partially or completely with the wrapper processed in Step 5 to prepare a moxa stick containing the oil and/or fat and the drug ingredient(s). The content of the oil and/or fat was 40%.

Still further, in Step 3, the steps that the mugwort floss and the wrapper were respectively brought into sufficient contact with the oil and/or fat processed in Step 2 were performed at the same time or performed stepwise.

Unique advantages: similar to the above-mentioned effects.

(7) A Seventh Preparation Method for a Moxa Stick

Preparation Steps:

Step 1: A moxa stick was prepared or a ready-made moxa stick was selected. Mugwort floss was wrapped with cotton paper and the like to prepare a stripe. According to whether moxa sticks contained drug(s), they were further divided into two types: ordinary pure moxa sticks and ordinary medicinal moxa sticks. The ordinary pure moxa sticks and the drug-containing ordinary medicinal moxa sticks all belonged to ordinary moxa sticks. For example, 24 gram of mugwort floss was taken (or 6 to 8 gram of drug powder was added) and tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form an ordinary pure moxa stick (or an ordinary medicinal moxa stick). According to the amount of the mugwort floss and the size of the cotton paper, ordinary moxa sticks of different sizes could be prepared. The ready-made moxa stick could also be bought directly from the market.

Step 2: The drug solution was brought into contact with the moxa stick. The drug(s) (for example, Chinese medicines such as Citri reticulatae pericarpium, Citri reticulatae pericarpium viride, Aurantii fructus immaturus, Aucklandiae radix, Aquilariae lignum resinatum) were brought into sufficient contact (the contacting manners included but were not limited to soaking, circulating flushing, and the like) with other liquid(s) (such as water and ethanol) other than oil and/or fat to prepare the drug solution, then the drug solution was brought into sufficient contact with the moxa stick (the contacting manners included but were not limited to soaking, circulating flushing, and the like). Said drug solution could also be ready-made drug(s) in a liquid state.

Step 3: The moxa stick processed in Step 2 was dried. The moxa stick processed in Step 2 was completely dried to prepare a dry medicinal moxa stick.

Step 4: The moxa stick processed in Step 3 was brought into contact with an oil and/or fat. The medicinal moxa stick processed in Step 3 was brought into sufficient contact (the contacting manners included but were not limited to soaking, circulating flushing, and the like) with the oil and/or fat (in usual cases, contacting for 1 hour or more was generally recommended), enabling the medicinal moxa stick to absorb the oil and/or fat sufficiently. According to experiments, the contacting time was preferably 5 hours or more.

Step 5: The moxa stick processed in Step 4 was taken out and dried partially to prepare a moxa stick containing the oil and/or fat and the drug ingredient(s).

Unique advantages: similar to the above-mentioned effects.

(8) A Eighth Preparation Method for a Moxa Stick, which Included:

Preparation Steps:

Step 1: A drug solution was brought into contact with mugwort floss to prepare mugwort floss containing drug ingredient(s). The drug(s) (for example, western medicines such as penicillin, cephalosporin, erythromycin, metronidazole, gentamicin) was brought into sufficient contact (the contacting manners included but were not limited to soaking, circulating flushing, and the like) with other liquid(s) (such as water and ethanol) other than oil and/or fat to prepare the drug solution, then the drug solution was brought into sufficient contact with the mugwort floss (the contacting manners included but were not limited to soaking, circulating flushing, and the like). Said drug solution could also be ready-made drug(s) in a liquid state.

Step 2: The mugwort floss processed in Step 1 was dried. The mugwort floss processed in Step 1 was completely dried to prepare dry mugwort floss containing the drug ingredient(s).

Step 3: The dry medicinal mugwort floss processed in Step 2 was prepared into a medicinal moxa stick. The dry medicinal mugwort floss processed in Step 2 was wrapped with cotton paper and the like to prepare a stripe. The moxa stick herein was a medicinal moxa stick containing drug(s). For example, 24 gram of said medicinal mugwort floss was taken and tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form the medicinal moxa stick. According to the amount of the medicinal mugwort floss and the size of the cotton paper, medicinal moxa sticks of different sizes could be prepared.

Step 4: The moxa stick processed in Step 3 was brought into contact with an oil and/or fat. The medicinal moxa stick processed in Step 3 was brought into sufficient contact (the contacting manners included but were not limited to soaking, circulating flushing, and the like) with the oil and/or fat (in usual cases, contacting for 1 hour or more was generally recommended), enabling the medicinal moxa stick to absorb the oil and/or fat sufficiently. According to experiments, the contacting time was preferably 5 hours or more.

Step 5: The moxa stick processed in Step 4 was taken out and dried partially to prepare a moxa stick containing the oil and/or fat and the drug ingredient(s).

Unique advantages: similar to the effects of the above-mentioned methods.

In addition to soaking, circulating flushing could also be used as the contacting manners. A device which could enable oil and/or fat to flow circularly was made, and the drug(s) and the moxa stick were put in a certain segment of the circulating device, and the effects of contacting with the flowing oil and/or fat sufficiently were achieved.

The manner of drip filling could also be used. The mugwort floss or the moxa stick was drip filled with oil and/or fat containing the drug ingredient(s) to prepare a novel medicinal moxa stick.

Other contacting manners could also be used for preparation.

(9) Prepare a Novel Medicinal Moxa Stick with Essential Oils

Preparation method: Step 1: Tea oil containing essential oil ingredients was prepared. 500 ml of tea oil was taken, 2 ml of Angelicae Sinensis Radix essential oil, 2 ml of Angelicae Dahuricae Radix essential oil, 2 ml of Zanthoxyli Pericarpium essential oil, 2 ml of Litsea Cubeba essential oil, 2 ml of orange essential oil and 2 ml of fennel essential oil were added. The mixture was stirred to mix evenly to prepare the tea oil containing essential oil ingredients.

Step 2: A pure moxa stick was prepared (it could be bought from the market directly). Generally, 24 gram of mugwort floss was taken and tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form the pure moxa stick. According to the amount of the mugwort floss and the size of the cotton paper, moxa sticks of different sizes could be prepared.

Step 3: The pure moxa stick was soaked with the tea oil containing essential oil ingredients. The pure moxa stick prepared in Step 2 was soaked with the tea oil containing essential oil ingredients prepared in Step 1 for 5 to 10 hours, so that the soaking was sufficient. The pure moxa stick was taken out and dried in shade naturally till the content of the oil and/or fat was 50%, thus a novel medicinal moxa stick was prepared. About 10 moxa sticks could be soaked in 500 g of the tea oil in Step 1.

Application method: Step 1: The novel medicinal moxa stick was ignited by a fire source such as a butter lamp, a candle and a lighter, enabling it to burn for approximately 10 seconds. Step 2: A 6-layer napkin or straw paper was used to prepare a simple cover for moxibustion, with which the novel medicinal moxa stick was wrapped so that the open fire was extinguished. Step 3: The novel medicinal moxa stick was held in hand to give moxibustion, so as to treat gastrointestinal diseases such as cholera, vomiting and diarrhoea. According to the different functions of essential oils, different oils and/or fats could also be combined to prepare the novel medicinal moxa stick for other uses.

(10) Prepare a Novel Medicinal Moxa Stick by Soaking a Medicinal Moxa Stick with Lard Oil Preparation Method Step 1: A medicinal moxa stick was prepared (it could be bought from the market directly). For example, generally, 24 gram of mugwort floss was taken and drug(s) was incorporated into the mugwort floss (for example, 6 to 8 gram of drug powder was added, or other weight of drug powder was added, and the drug powder was mixed well with the mugwort floss). The mugwort floss and the drug powder were tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form the medicinal moxa stick. According to the amount of the mugwort floss and the drug(s) and the size of the cotton paper, medicinal moxa sticks of different sizes could be prepared.

Step 2: The medicinal moxa stick processed in Step 1 was soaked with lard oil. 500 g of lard oil was taken. When the lard oil was in a liquid state at a constant temperature of 48° C., the medicinal moxa stick processed in Step 1 was added, soaked for 5 to 10 hours, taken out to dry in shade till the content of lard oil accounted for 70%, thus a novel medicinal moxa stick was prepared.

Application method: Step 1: The novel medicinal moxa stick was ignited by a fire source such as a butter lamp, a candle and a lighter, enabling it to burn for approximately 10 seconds. Step 2: A 6-layer napkin or straw paper was used to prepare a simple cover for moxibustion, with which the novel medicinal moxa stick was wrapped so that the open fire was extinguished. Step 3: The novel medicinal moxa stick was held in hand to give moxibustion.

(11) Prepare a Moxa Stick Containing Oil and/or Fat Preparation Method

Step 1: A pure moxa stick was prepared (it could be bought from the market directly). Generally, 24 gram of mugwort floss was taken and tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form the pure moxa stick. According to the amount of the mugwort floss and the size of the cotton paper, moxa sticks of different sizes could be prepared.

Step 2: The moxa stick processed in Step 1 was soaked with tea oil. 500 ml of tea oil was taken, 10 moxa sticks processed in Step 1 were added, soaked for 5 to 10 hours, taken out to dry in shade till the content of tea oil accounted for 60%.

Application method: Step 1: The moxa stick containing oil and/or fat was ignited by a fire source such as a butter lamp, a candle and a lighter, enabling it to burn for approximately 10 seconds. Step 2: A 6-layer napkin or straw paper was used to prepare a simple cover for moxibustion, with which the medicinal moxa stick containing oil and/or fat was wrapped so that the open fire was extinguished. Step 3: The moxa stick containing oil and/or fat was held in hand to give moxibustion.

It could be understood that the drug ingredient(s) were not essential but were added as needed. Even if no drug ingredient was added, the moxa stick containing oil and/or fat itself could also achieve effects similar and superior to that of the traditional moxibustion.

(12) Physical Structure and Ingredients of Each Part

The moxa stick included mugwort floss or other processed products of wormwood as well as an oil and/or fat. The processed products of wormwood absorbed said oil and/or fat via contact. The weight of said oil and/or fat accounted for 10% or more of the total weight of the moxa stick, said oil and/or fat was a vegetable oil and/or fat, an animal oil and/or fat, a processed product of vegetable oil(s) or a processed product of animal oil and/or fat.

The medicinal moxa stick included mugwort floss or other processed products of wormwood, drug ingredient(s), and animal oil(s) (or vegetable oil(s)). The mugwort floss absorbed animal oil(s) by being soaking with the animal oil(s), and after being dried partially, the weight of the animal oil(s) accounted for 10% or more of the total weight of the moxa stick, said animal oil was lard oil, badger oil, sheep oil, etc. The drugs could be dissolved in animal oil(s) in advance, the moxa stick or the mugwort floss could be soaked, drip filled, flushed, or sprayed with animal oil(s); the drugs could also be dissolved in other solvents, the moxa stick or the mugwort floss was soaked, drip filled, flushed, or sprayed with drug solution, and after being dried, the moxa stick or the mugwort floss was soaked, drip filled, flushed, or sprayed again with pure animal oil(s); the drugs could also be added to the moxa stick directly in powder, granules, and bulks, and the moxa stick was soaked, drip filled, flushed, or sprayed with animal oil(s). Thus, the drug(s) were made to distribute evenly in the moxa stick, and the animal oil(s) was also made to distribute evenly in the moxa stick. After absorbing the animal oil(s), the moxa stick was dried in shade (other manners of drying such as spin-drying, drying in the air could also be adopted), ensuring that the prepared moxa stick remained in a wet state that was incompletely dry, such that the prepared moxa stick could be easily wrapped and extinguished after being ignited by dry paper. The temperature of the preparation process was adjusted to the solidifying point(s) of the animal oil(s) or higher to ensure that the animal oil(s) was in a liquid state in the preparation process.

The processed products of wormwood may be mugwort floss, or Blumea balsamifera powder, or the processed products of wormwood mixed with other materials, as well as all other processed products containing wormwood. Mugwort floss is the most common processed product of wormwood, and refers to the velvet-like substance processed and prepared from Artemisiae Argyi Folium. The commonly used oil and/or fat are, for example, a vegetable oil and/or fat such as tea oil, sunflower oil, olive oil, sesame oil, peanut oil, rapeseed oil, palm oil, soybean oil, tung oil, corn oil and castor oil, an animal oil and/or fat such as lard oil, badger oil, sheep oil and beef lard, a processed product of oil and/or fat such as refined oil, mixed oil and blend oil.

The moxa stick may be prepared by wrapping mugwort floss with paper, cloth, and the like, or the moxa stick is prepared directly by mixing mugwort floss with viscous substance without the need of wrapping, or the moxa stick is prepared by extruding mugwort floss with an external force. The common moxa stick includes cladding(s) and an inner core portion, the inner core portion is wrapped with the cladding(s). The cladding(s) may be a single layer or multiple layers.

The moxa stick may also contain the drug ingredient(s) dissolved in oil and/or fat. Drugs refer to substances that are used to prevent, treat and diagnose human diseases, regulate the physiological function of human purposefully, and that have specified indications or major functions, methods of administration and dosages, including Chinese medicinal materials, Chinese medicine decoction pieces, Chinese patent medicines, chemical raw medicines, etc.

The drug(s) used during the preparation of the novel medicinal moxa stick may be a certain kind of drug, and may also be a combination of drugs formed by two or more drugs. By the manner that first enabling the oil and/or fat to absorb the effective drug ingredients and then enabling the moxa stick to absorb the oil and/or fat, the moxa stick may contain the effective ingredient(s) of the drug(s). When in use, the drug ingredient(s) come into contact with the skin along with the permeation of the oil and/or fat to produce therapeutic effect. Therefore, all the drugs whose effective ingredients are soluble in the oil and/or fat may be used in the present disclosure, and there is no need to limit the type of drugs.

The material of the wrapper may be paper, which includes cotton paper, Chinese art paper, kraft paper, straw paper, as well as other paper suitable for preparing the moxa stick. Other materials suitable for preparing the moxa stick (such as cotton cloth) may also be used for the cladding(s).

The most common material of the wrapper is cotton paper. Cotton paper is paper made of fibers such as bark, yarn bark, barks of wild plants and vegetable gums. Said paper is white, soft and tough, and the fibers are thin and long as cotton, thereby being referred to as cotton paper, such as mulberry paper.

A specially matched cover for moxibustion is not essential for the present disclosure. When the moxa stick of the present disclosure is used, the cover for moxibustion may be made by selecting paper or cloth which is common in life by oneself as needed to replace the matched cover for moxibustion. Then, the ignited moxa stick is wrapped, and moxibustion is given after extinguishing the open fire of the moxa stick.

A moxibustion equipment, which includes a moxa stick and a cover for moxibustion; the moxa stick includes processed product(s) of wormwood, drug ingredient by oneself and an oil and/or fat; the processed product(s) of wormwood absorbs said oil and/or fat via contact; the weight of said oil and/or fat accounts for 10% or more of the total weight of the moxa stick, said oil and/or fat is a vegetable oil and/or fat, an animal oil and/or fat, a processed product of vegetable oil and/or fat or a processed product of animal oil and/or fat. The drug ingredient(s) are added through three routes: the moxa stick has already been a medicinal moxa stick containing drug powder before contacting with the oil and/or fat, or the moxa stick is first brought into contact with the drug solution to absorb the drug ingredients before contacting with the oil and/or fat, or the moxa stick is brought into contact with the oil and/or fat containing the drug ingredient(s) to absorb the drug ingredient(s). When in use, the cover for moxibustion is used to wrap the moxa stick after burning to extinguish the open fire of the moxa stick, and used as the spacer between the moxa stick and the skin of human body.

The material of the cover for moxibustion is paper, cloth, or other processed products of plant fiber. There is a control device used to control the size of the opening at the opening of the cover for moxibustion, the control device may be one or more of a string, a rubber band, a clip or a metal ring. Also, the cover for moxibustion may not be provided with a specialized control device for controlling the size of the opening, and controlling the size of the opening is achieved by clutching tightly by hand instead. According to experiments, the content of the oil and/or fat in the moxa stick was 10% or more, and 20% to 70% was a preferred example. When the content of the oil and/or fat was higher than 70%, oil(s) was easy to drip and cause scald at the time of application. When the content of the oil and/or fat was lower than 20%, it was not easy for a small amount of the oil and/or fat to permeate out, and the permeation of a small amount of oil and/or fat was favorable for the direct contact of the drug ingredient(s) in the oil and/or fat with the skin. A more preferred example was 50% to 60% for the content of the oil and/or fat in the moxa stick.

Cotton paper is paper made of fibers such as bark, yarn bark, barks of wild plants and vegetable gums. Said paper is white, soft and tough, and the fibers are thin and long as cotton, thereby being referred to as cotton paper, such as mulberry paper. The cotton paper in the novel medicinal moxa stick has already sufficiently absorbed the oil and/or fat containing the drug ingredients, which is different from the cotton paper in the ordinary moxa stick.

The mugwort floss refers to the velvet-like substance processed and prepared from Artemisiae Argyi Folium. According to whether drugs are mixed, mugwort floss is divided into two types: pure mugwort floss and medicinal mugwort floss. The pure mugwort floss and the medicinal mugwort floss containing drug(s) all belong to mugwort floss.

The mugwort floss in the novel medicinal moxa stick has already sufficiently absorbed the oil and/or fat containing the drug ingredient(s), and is different from mugwort floss in the ordinary moxa stick.

Oil and/or fat is a generic name for fatty oils and fats, and the main ingredients of the oil and/or fat are the glycerides of fatty acids. Under room temperature, the oil and/or fat is referred to as lipids or fats if it is in a solid or semi-solid state, and is referred to as oils or fatty oils if it is in a liquid state. The advantages of soaking with the oil and/or fat are as follows. (1) The oil and/or fat is not easy to volatilize, has better durability and is shelf-stable as compared with other liquids. For example, a liquid containing alcohol(s) has a much higher volatility and is not easy to preserve. (2) Characteristic as media (extractability). The oil and/or fat may serve as the carriers of the effective drug ingredients, by soaking the drug(s) in the oil and/or fat, the effective ingredient(s) in the drug(s) may be dissolved into the oil and/or fat, and the oil and/or fat are absorbed by mugwort floss, enabling the mugwort floss to carry the effective drug ingredient(s) in the oil and/or fat as well without increasing the proportion of the non-mugwort floss solid substance in the moxa stick. (3) The oil and/or fat is easy to precipitate and permeate when being heated, and is easy to permeate into part of the media (including but not limited to paper, cotton cloth, etc.) after being burned or heated.

If the novel medicinal moxa stick is prepared with a lipid which is solid or semi-solid under room temperature, the temperature needs to be elevated to keep the lipid in a liquid state in the preparation process. The novel medicinal moxa stick may be prepared with one kind of oil and/or fat, the mixed oil and/or fat formed by two or more kinds of oil and/or fat may also be used, the mixed liquid mainly comprised of oil and/or fat may also be used, said mixed liquid is formed by adding other liquids (such as water, alcohol and other liquids) other than oil and/or fat additionally to the oil and/or fat or the mixed oil and/or fat.

The drug ingredient(s) absorbed by the oil and/or fat refer to the drug ingredient(s) absorbed after drug(s) were soaked with the oil and/or fat. Drugs refer to substances that are used to prevent, treat and diagnose human diseases, regulate the physiological function of human purposefully, and that have specified indications or major functions, methods of administration and dosages, including Chinese medicinal materials, Chinese medicine decoction pieces, Chinese patent medicines, chemical raw medicines, etc. The drug(s) used during the preparation of the novel medicinal moxa stick may be a certain kind of drug, and may also be a combination of drugs formed by two or more drugs.

When preparing the moxa stick, the drug ingredient(s) come into contact with the skin with the permeation of the oil and/or fat to produce therapeutic effect. Therefore, all the drug(s) whose effective ingredient(s) are soluble in the oil and/or fat may be used in the present disclosure, and there is no need to limit the type of drugs. The drug(s) include but are not limited to the following types.

The drug(s) of the present disclosure include various Chinese medicines, western medicines, and the like: diaphoretics such as Ephedrae Herba, Cinnamomi Ramulus, Perilla Frutescens, Zingiberis Rhizoma Recens, Moslae Herba, Schizonepetae Herba, Saposhnikoviae Radix, Notopterygii Rhizoma et Radix, Angelicae Dahuricae Radix, Asari Radix et Rhizoma, Ligustici Rhizoma et Radix, Xanthii Fructus, Magnoliae Flos, Fistular Onion Stalk, Centipedae Herba, Coriander, Chinese Tamarisk, Menthae Haplocalycis Herba, Arctii Fructus, Cicadae Periostracum, Mori Folltfm, Chrysanthemi Flos, Viticis Fructus, Bupleuri Radix, Cimicifugae Rhizoma, Puerariae Lobatae Radix, Sojae Semen Praeparatum, etc.; antipyretics such as Gypsum Fibrosum, crystalline mirabilite, Anemarrhenae Rhizoma, Phragmitis Rhizoma, Trichosanthis Radix, Gardeniae Fructus, Prunellae Spica, Cassiae Semen, Eriocauli Flos, Buddlejae Flos, Celosiae Semen, Scutellariae Radix, Coptidis Rhizoma, Phellodendri Chinensis Cortex, Gentianae Radix et Rhizoma, Fraxini Cortex, Sophorae Flavescentis Radix, Dictamni Cortex, Lonicerae Japonicae Flos, Forsythiae Fructus, Andrographis Herba, Isatidis Folium, Isatidis Radix, Indigo Naturalis, Cyrtomium Fortunei, Taraxaci Herba, Violae Herba, Chrysanthemi Indici Flos, Paridis Rhizoma, Bistortae Rhizoma, Rhapontici Radix, Smilacis Glabrae Rhizoma, Houttuyniae Herba, Fagopyri Dibotryis Rhizoma, Sargentodoxae Caulis, Herba Patriniae, Belamcandae Rhizoma, Sophorae Tonkinensis Radix et Rhizoma, Lasiosphaera Calvatia, Canarii Fructus, Physalis Calyx seu Fructus, Bruceae Fructus, Lobeliae Chinensis Herba, Hedyotis Diffusa Willd, Cremastrae Pseudobulbus Pleiones Pseudobulbus, Radix Rehmanniae, Scrophulariae Radix, Moutan Cortex, Paeoniae Radix Rubra, Amebiae Radix, Flos Hibisci Mutabilis, Folium Hibisci Mutabilis, Artemisiae Annuae Herba, Cynanchi Atrati Radix et Rhizoma, Lycii Cortex, Stellariae Radix, Picrorhizae Rhizoma, Spirodelae Herba, Equiseti Hiemalis Herba, etc: purgatives such as Rhei Radix et Rhizoma, Natrii Sulfas, Sennae Folium, Aloe, Cannabis Fructus, Pruni Semen, Kansui Radix, Euphorbiae Pekinensis Radix, Genkwa Flos, Phytolaccae Radix, Pharbitidis Semen, Crotonis Fructus, Euphorbiae Semen, etc.; antirheumatics such as Angelicae Pubescentis Radix, Clematidis Radix et Rhizoma, Aconiti Radix, Agkistrodon, Zaocys, Chaenomelis Fructus, silkworm excrement, Lycopodii Herba, Herba Aristolochiae Mollissimae, Pine Nodular Branch, Piperis Kadsurae Caulis, Sinomenii Caulis, Erycibes Caulis, Tripterygium Hypoglaucum Hutch, Shortstalk Monkshood Root, Liquidambaris Fructus, Gentianae Macrophyllae Radix, Stephaniae Tetrandrae Radix, Mori Ramulus, Siegesbeckiae Herba, Harlequin Glorybower leaf and twig, bark of Himalayan Coralbean, Trachelospermi Caulis et Folium, Tripterygium Wilfordii Hook, Erodii Herba Geranii Herba, Dioscoreae Nipponicae Rhizoma, Luffae Fructus Retinervus, Acanthopanacis Cortex, Taxilli Herba, Cibotii Rhizoma, Homalomenae Rhizoma, Saussurea Involucrata, Pyrolae Herba, Folium Photiniae; dampness-resolving drugs such as Agastache Rugosa, Eupatorii Herba, Atractylodis Rhizoma, Magnoliae Officinalis Cortex, Amomi Fructus, Amomi Fructus Rotundus, Alpiniae Katsumadai Semen, Tsaoko Fructus, etc.; diuretics for eliminating dampness such as Poria, Coicis Semen, Polyporus, Alismatis Rhizoma, Benincasae Exocarpium, corn silk, Calabash, Periplocae Cortex, Semen Hoveniae, Euphorbia Helioscopia, Mole Cricket, Capsella, Plantaginis Semen, Talcum, Akebiae Caulis, Tetrapanacis Medulla, Dianthi Herba, Herba Polygoni Avicularis, Kochiae Fructus, Lygodii Spora, Pyrrosiae Folium, Fructus Malvae, Junci Medulla, Rhizoma Dioscoreae Hypoglaucae, Artemisiae Scopariae Herba, Lysimachiae Herba, Polygoni Cuspidati Rhizoma et Radix, Hypericum Japonicum, Sedi Herba, Abriherba, Herba Phyllanthi Urinariae, etc.; interior-warming drugs such as Aconiti Lateralis Radix Praeparaia, Zingiberis Rhizoma, Cinnamomi Cortex, Euodiae Fructus, Foeniculi Fructus, Caryophylli Flos, Alpiniae Officinarum Rhizoma, Piperis Fructus, Zanthoxyli Pericarpium, Piperis Longi Fructus, Litseae Fructus, etc.; qi-regulating drugs such as Citri Reticulatae Pericarpium, Citri Reticulatae Pericarpium Viride, Aurantii Fructus Immaturus, Aucklandiae Radix, Aquilariae Lignum Resinatum, Santali Albi Lignum, Toosendan Fructus, Linderae Radix, Aristolochia Debilis, Litchi Semen, Cyperi Rhizoma, Citri Sarcodactylis Fructus, Citri Fructus, Rosae Rugosae Flos, Armeniaca Mume, Aesculi Semen, Allii Macrostemonis Bulbu, Aristolochiae Herba, Arecae Pericarpium, Nardostachyos Radix et Rhizoma, Aspongopus, Canavaliae Semen, etc.; digestant drugs such as Crataegi Fructus, Medicated Leaven, Hordei Fructus Germinatus, Oryzae Fructus Germinatus, Raphani Semen, Galli Gigerii Endothelium Comeum, Herba Paederiae, root of Wilford Swallowwvort, Ferulae Resina, etc.; anthelmintics such as Quisqualis Fructus, Meliae Cortex, Arecae Semen, Semen Cucurbitae, Gemma Agrimoniae, Omphalia, Carpesii Fructus, Torrevae Semen, Ulmus Macrocarpa Hance: hemostatics such as Common Cephalanoplos Herb, Cirsii Japonici Herba, Sanguisorbae Radix, Sophorae Flos, Platycladi Cacumen, Imperatae Rhizoma, Radix Boehmeriae, Radix Rumicis Japonici, Notoginseng Radix et Rhizoma, Rubiae Radix et Rhizoma, Typhae Pollen, Ophicalcitum, Dalbergiae Odoriferae Lignum, Bletillae Rhizoma, Agrimoniae Herba, beautyberry, Crinis Trachycarpi, Crinis Carbonisatus, Nelumbinis Rhizomatis Nodus, Loropetalum Chinense, Zingiberis Rhizoma Praeparatum, etc.; drugs for invigorating blood circulation and eliminating stasis such as Chuanxiong Rhizoma, Corydalis Rhizoma, Curcumae Radix, Curcumae Longae Rhizoma, Olibanum, Myrrha, Faeces Trogopterorum, Corydalis Decumbentis Rhizoma, Liquidambaris Resina, Salviae Miltiorrhizae Radix et Rhizoma, Carthami Flos, Persicae Semen, Leonuri Herba, Lycopi Herba, Achyranthis Bidentatae Radix, Spatholobi Caulis, Vaccariae Semen, Rosae Chinensis Flos, Campsis Flos, Eupolyphaga Steleophaga, Strychni Semen, Pyrite, Sappan Lignum, Drynariae Rhizoma, Draconis Sanguis, Catechu, Diverse Wormwood Herb, Curcumae Rhizoma, Sparganii Rhizoma, Hirudo, Gadfly, Mylabris, Manis Squama, etc.; drugs for resolving phlegm and Relieving cough and asthma such as Pinelliae Rhizoma, Arisaematis Rhizoma, Rhizoma Typhonii, white mustard seed, Chinese honey locust, Inulae Flos, Cynanchi Stauntonii Rhizoma et Radix, Ranunculi Temati Radix, Fritillariae Cirrhosae Bulbus, Fritillariae Thunbergii Bulbus, Trichosanthis Fructus, Bambusae Caulis In Taenias, Succus Bambusae, Bambusae Concretio Silicea, Peucedani Radix, Platycodonis Radix, Sterculiae Lychnophorae Semen, Sargassum, Laminariae Thallus Eckloniae Thallus, Rhizoma Dioscoreae Bulbiferae, Concha Meretricis seu Cyclinae, Bryozoatum, Arcae Concha, Micacolorata, Armeniacae Semen Amarum, Perillae Fructus, Stemonae Radix, Asteris Radix et Rhizoma, Farfarae Flos, Aristolochiae Fructus, Eriobotryae Folium, Mori Cortex, Descurainiae Semen Lepidii Semen, Ginkgo Semen, Ardisiae Japonicae Herba, Daturae Flos, Physochlainae Radix, Rhododendri Daurici Folium, etc.; sedatives and tranquilizers such as Cinnabaris, Magnetitum, Fossilizid, Amber, Ziziphi Spinosae Semen, Platycladi Semen, Ganoderma, Valerian Root, Polygoni Multiflori Caulis, Albiziae Cortex, Polygalae Radix, etc.; drugs for calming liver to stop endogenous wind such as Haliotidis concha, Margaritifera concha, Ostreae concha, Concha mauritiae, Hematite, Tribulus terrestris, Apocyni veneti folium, Ferrosic Oxide, Saigae tataricae comu, Bovis calculus, Margarita, Uncariae ramulus cum uncis, Gastrodiae rhizoma, Pheretima, Scorpio, Scolopendra, Bombyx batryticatus, etc.; drugs for inducing resuscitation such as Moschus, Bomeolum Syntheticum, Styrax, Acori Tatarinowii Rhizoma, etc.; tonic drugs such as Ginseng Radix et Rhizoma, Panacis Quinquefolii Radix, Codonopsis Radix, Pseudostellariae Radix, Astragali Radix, Atractylodis Macrocephalae Rhizoma, Dioscoreae Rhizoma Lablab Semen Album, Glycyrrhizae Radix et Rhizoma, Jujubae Fructus, Acanthopanacis Senticosi Radix et Rhizoma seu Caulis, Herba Gynostemmatis Pentaphylli, Rhodiolae Crenulatae Radix et Rhizoma, Hippophae Fructus, Cervi Comu Pantotrichum, Placenta Hominis, Epimedii Folium, Morindae Officinalis Radix, Curculiginis Rhizoma, Eucommiae Cortex, Dipsaci Radix, Cistanches Herba, Cynomorii Herba, Psoraleae Fructus, Fructus Alpinae Oxyphyllae, Cuscutae Semen, Astragali Complanati Semen, Gecko, Juglandis Semen, Cordyceps, Trigonellae Semen, Semen Allii Tuberosi, actinolite, Fluoritum, ursine seal's penis and teste, Hippocampus, Ranae Oviductus, Pimpinella Thettungiana, Angelicae Sinensis Radix, prepared Radix Rehmanniae, Paeoniae Radix Alba, Polygoni Multiflori Radix, Broussonetiae Fructus, Glehniae Radix, Adenophorae Radix, Lilii Bulbus, Ophiopogonis Radix, Asparagi Radix, Dendrobii Caulis, Polygonati Odorati Rhizoma, Polygonati Rhizoma, Changii Radix, Lycii Fructus, Ecliptae Herba, Ligustri Lucidi Fructus, Mori Fructus, Sesami Semen Nigrum, Testudinis Carapax et Plastrum, Trionycis Carapax; astringents such as Ephedrae Radix et Rhizoma, Fructus Tritici Levis, rhizome and root of Glutinous Rice, Schisandrae Chinensis Fructus, Mume Fructus, Galla Chinensis, Papaveris Pericarpium, Chebulae Fructus, Granati Pericarpium, Myristicae Semen, Halloysitum Rubrum, Limonitum, Comifructus, Rubi Fructus, Mantidis OOtheca, Rosae Laevigatae Fructus, Sepiae Endoconcha, Nelumbinis Semen, Euryales Semen, hedgehog skin, Ailanthi Cortex, Celosiae Cristatae Flos, etc.; emetics such as Dichroae Radix, muskmelon fruit pedicel, chalcanthite, etc.; insecticidal and antipruritic drugs for counteracting toxic substances such as Realgar, Sulfur, Alumen, Cnidii Fructus, Bufonis Venenum, camphor, Momordicae Semen, Pseudolaricis Cortex, Vespae Nidus, Allii Sativi Bulbus, etc.; drugs for drawing out poison, eliminating putridity and engendering flesh such as hydrargyrum oxydatum crudum, Calomelas, arsenolite, minium, Calamina, borax, etc.; antibiotics such as penicillin, cephalosporin, erythromycin, metronidazole, gentamicin, terramycin, etc; Chinese herb extracts such as berberine, artemisinin, ephedrine, etc.; essential oils such as Angelicae Sinensis Radix essential oil, Angelicae Dahuricae Radix essential oil, Zanthoxyli Pericarpium essential oil, Litsea Cubeba essential oil, orange essential oil, fennel essential oil, etc.

The advantages of the products of the examples were as follows. (1) Since the above oils and/or fats containing the drug ingredients were adopted, as compared with the ordinary medicinal moxa sticks (for example, thunder-fire miraculous moxa sticks and taiyi miraculous moxa sticks), the problem that the drug powder might not be distributed evenly was solved, and the effect of the uniform distribution of the drug ingredients was achieved. (2) Since the above oils and/or fats containing the drug ingredients were adopted, as compared with the ordinary medicinal moxa sticks (for example, thunder-fire miraculous moxa sticks and taiyi miraculous moxa sticks), the problem that the content of the drug powder might be too high was solved, and the effect of not increasing the powdery solid ingredients was achieved. (3) Since the adopted content of the above oils and/or fats was 10% or more, in other words, the medicinal moxa sticks were not dry, they could be extinguished instantly with straw paper, napkin, cloth, and the like at the time of burning. As compared with the ordinary moxa sticks, the problem that burning was needed all the time during the application process was solved, and the effects of stopping burning during the application process and reducing scald to the maximum extent were achieved. (4) The problem that a large amount of smoke was generated was solved, and the effects of saving energy and protecting environment as well as reducing the harm to human body were achieved. (5) The problem that the fire of moxa tended to be hot and dry and was easy to cause excessive internal heat in body was solved, and the effect that the heat was gentle and lasting was achieved. (6) In other words, the medicinal moxa sticks were not dry, after the fire was extinguished instantly by wrapping the medicinal moxa sticks with straw paper, napkin, cloth, and the like, a small amount of oils and/or fats might permeate and flow out to contact with the skin of the people who received moxibustion. As compared with the ordinary medicinal moxa sticks, the problem that the effective drug ingredients could not be brought into contact with the skin and thus leading to difficulty) in achieving effects was solved, and the effect that the effective ingredients of drugs permeated to the skin directly via the permeated oils and/or fats was achieved.

Application Steps:

Step 1: Ignition. The novel medicinal moxa stick was ignited by a fire source such as a lighter, an oil lamp and a candle.

Step 2: Moxibustion was given after the fire was extinguished by wrapping the novel medicinal moxa stick with the cover for moxibustion. The cover for moxibustion was made into a pan-shaped one with soft, air-permeable and dry straw paper, napkin, cotton cloth, or the like. The burning end of the novel medicinal moxa stick was wrapped with the cover for moxibustion to extinguish the fire instantly, the cover for moxibustion was clutched tightly, and then the novel medicinal moxa stick was held in hand to give moxibustion.

Although the open fire could not be seen when the traditional moxa stick is used to give moxibustion, moxa stick actually continued to burn in the form of charcoal fire. Since the novel medicinal moxa stick contained a certain proportion of liquid, straw paper, napkin, and the like were not soaked with clear water before use, with which the novel medicinal moxa stick could be wrapped directly and the fire was extinguished instantly, and there was no burning charcoal fire or sparks any more. The cover for moxibustion was not fixed on the body, and was wrapped on the novel medicinal moxa stick directly instead, thus being able to give moxibustion to multiple acupoints continuously, for example, give moxibustion to multiple acupoints along a certain meridian.

Therefore, the examples had the following advantages. (1) The heat was similar to that of the scarring moxibustion. As compared with the suspended moxibustion and the moxibustion by warming moxibustion apparatus, the problem that the heat was not enough due to the distance was solved, and the effect of retaining the heat to the maximum extent was achieved. (2) As compared with the other traditional moxibustion methods other than the needle warming moxibustion, the problem that it was hard to give moxibustion to arbitrary acupoint all over the body (for example, armpit and perineum acupoint) accurately was solved, and the effect that arbitrary acupoint all over the body could be given moxibustion accurately was achieved. (3) As compared with other traditional moxibustion methods other than the needle warming moxibustion, the problem that multiple acupoints could not be given moxibustion continuously was solved, and the effect of being able to give moxibustion to multiple acupoints continuously (for example, giving moxibustion to multiple acupoints along a certain meridian) was achieved. (4) Burning was stopped at the time of application. As compared with other traditional moxibustion methods, the problem that it was burning all the time during the application process was solved, the effect of safety was achieved, and the sense of fear of people who received moxibustion was greatly reduced at the same time. (5) Burning was stopped at the time of application. As compared with other traditional moxibustion methods, the problem that it was burning all the time during the application process was solved, and the effect of protecting the environment was achieved. (6) Burning was stopped at the time of application.

As compared with other traditional moxibustion methods, the problems that large amount of smoke was generated and might do harm to the health of people who gave moxibustion and people who received moxibustion were solved, and the effect of being beneficial to health was achieved. (7) People who received moxibustion did not have the sensation of acute pain, and there was no need for the people who received moxibustion to keep a certain fixed pose for a long time to receive moxibustion. The psychological pressure due to receiving moxibustion was also eliminated. As compared with most other moxibustion methods, the problem that the psychological pressure was caused in people who received moxibustion was solved, and the effect of enhancing the comfort degree of people who received moxibustion was achieved. (8) As compared with other moxibustion methods such as needle warming moxibustion, the difficulty of operation was reduced, and the effect of easy popularization was achieved. (9) The oils and/or fats carrying the effective drug ingredients in the novel moxa sticks permeated out properly and contacted with the skin surface of the acupoints of moxibustion. As compared with most other moxibustion methods, the permeation of the effective drug ingredients was enhanced, and the nourishment function for the skin of human body was increased at the same time.

The above multiple examples may achieve the following technical effects correspondingly.

(1) In the examples, the moxa sticks contained oils and/or fats, and were partially dried. If the moxa sticks were ignited directly and used without being dried, oils might drip during the application process. Therefore, the moxa sticks containing partially dried oils and/or fats were safer, and it was more convenient to use since there was no need to carry the oils and/or fats additionally at the time of application, for example, it could pass through the security check at airports.

(2) Instead of simply adding drug powder, only by contacting the moxa sticks, oils and/or fats and drugs with each other, the drug ingredients were dissolved in the oils and/or fats, and the novel medicinal moxa sticks were prepared. This completely changed the route of adding the drug ingredients in the preparation process of the medicinal moxa stick and simplified the preparation process.

(3) The drug ingredients were dissolved in oils and/or fats so that the drug ingredients were in an invisible state and distributed evenly in the novel medicinal moxa sticks. The problem, which was the uneven distribution of the drug powder possibly due to insufficient stirring in the medicinal moxa sticks traditionally prepared by adding the drug powder, would not appear.

(4) The drug ingredients were dissolved in oils and/or fats so that the drug ingredients were in an invisible state and the visible ingredients were not increased, and the problem that other ingredients other than mugwort floss in the medicinal moxa stick traditionally prepared by adding the drug powder were possibly excessive was solved. According to the historical literature, materials other than moxa often produce blazing fire after burning as the material of moxibustion, which is harmful to human body. As described in "Yellow Emperor's Classic of Internal Medicine (also referred to as Huangdi Neijing)", "Qi is weak when the fire is strong, while Qi is strong when the fire is less", indicating that the mild fire is beneficial to health while the blazing fire does harm to the body.

(5) In the examples, the medicinal moxa sticks contained 10% or more of the oils and/or fats, and were in an incompletely dry state. At the time of burning, the oils and/or fats in a liquid state contributed to extinguishing the fire instantly with dry paper or cloth while the fire could not be extinguished instantly with dry paper or cloth when the ordinary moxa stick in a dry state was burning. This enhanced the safety of the novel medicinal moxa sticks, reduced the possibility of scald and fire disaster, and enhanced the comfort degree of people who received moxibustion at the same time, thus making it possible for the moxa stick to contact with the skin at a short distance.

(6) In the examples, the moxa sticks contained 10% or more of the oils and/or fats, and was in an incompletely dry state. At the time of burning, the oils and/or fats in a liquid state contributed to extinguishing the fire instantly with dry paper or cloth, and continuous burning was not needed during the application process. The problem that large amount of smoke was generated during the application process of the ordinary moxa sticks was solved, and the pollution to the environment and the harm to the human respiratory system caused by the large amount of smoke were avoided. This was because the burning time of the open fire was very short and large amount of materials were saved.

(7) In the examples, the medicinal moxa sticks contained 10% or more of the oils and/or fats, and was in an incompletely dry state. After burning for a short period of time and being wrapped with dry paper or cloth to extinguish the fire, a small amount of oils and/or fats might permeate out without forming oil droplets. The medicinal moxa sticks contacted the skin of people who received moxibustion directly. By controlling the frequency of lifting and pressing to change the contacting time with the skin of people who received moxibustion, it was very easy to prevent scald, and the problem that the drug ingredients in the ordinary medicinal moxa sticks could not contact the skin directly and thus being hard to achieve effects was solved. People who gave moxibustion controlled the contacting time of the novel medicinal moxa sticks wrapped with dry paper or cloth with the skin by controlling the frequency of lifting and pressing, and the scald that might appear could be avoided effectively.

(8) In the examples, the medicinal moxa sticks/moxa sticks contained 10% or more of the oils and/or fats, and were in an incompletely dry state. This enabled the fire to be mild at the time of burning, and hot and dry charcoal fire which was produced when the dry moxa sticks were burning would not be produced. This mild fire was more beneficial to human health and was not easy to cause excessive internal heat (also referred to as yeet hey or yit hei) in people who received moxibustion. Still, since a small amount of oils and/or fats permeated out at the time of burning, hot and dry charcoal fire which caused the dry skin of people who received moxibustion would not be produced as in the case of burning the dry moxa sticks. As clearly indicated in "Yellow Emperor's Classic of Internal Medicine (also referred to as Huangdi Neijing)", "Less fire produces Qi", indicating that the mild fire is able to contribute to the healthy Qi of human. If the content of the oil and/or fat was too low such that the moxa stick was almost completely dry after being brought into contact with the oil and/or fat, then dry paper or cloth could not be used to extinguish the fire instantly and moxibustion could not be performed at a short distance. The moxa stick was burning all the time during the application process, which was neither safe nor environmentally friendly, and was inconvenient to use.

(9) In the examples, after the moxa sticks burned for a short period of time and were wrapped with dry paper or cloth to extinguish the fire, the remaining heat could be used to give moxibustion to multiple acupoints and moxibustion could be given to multiple acupoints along a certain meridian, which was rather clinically meaningful. Since the moxa sticks or mugwort floss was dry in the traditional moxibustion, at the time of burning, it was very hard to extinguish the fire instantly by wrapping the moxa stick or mugwort floss with dry substance, in general, the fire could only be extinguished by wrapping the moxa sticks or mugwort floss with a wet substance. However, if the fire was extinguished by wrapping the moxa sticks or mugwort floss with a wet substance, the heat would be greatly reduced and could hardly give moxibustion to multiple acupoints continuously.

(10) In the examples, after the moxa sticks burned for a short period of time, the fire was extinguished by wrapping the moxa sticks with dry paper or cloth, and moxibustion was given upon the dry paper or cloth. Moxibustion could be given to arbitrary acupoint all over the body accurately, which could not be achieved by the traditional moxibustion methods other than needle warming moxibustion.

(11) In the examples, the moxa sticks and dry paper or cloth were used in combination and the skin was contacted directly when being given moxibustion, which was beneficial to achieve the therapeutic effect rapidly, shortened the time of giving moxibustion, solved the problem that the moxibustion time of the suspended moxibustion and the moxibustion by warming moxibustion apparatus must be prolonged since the heat was insufficient due to the distance.

(12) In the examples, the moxa sticks and the cover for moxibustion (or simply several layers of dry paper or cloth) were used in combination. Ordinary people could perform the operation of giving moxibustion under the guidance of a physician. As compared with other moxibustion methods, it was convenient to operate and was safe, which was very beneficial for promotion and popularization.

(13) In the examples, the content of the oil and/or fat added in the moxa sticks was preferably 20% to 70%. The advantage of a content which was lower than 70% was that when using the moxa sticks, the oils would not drip to cause scald due to the excessive high content of the oils and/or fats, and the advantage of a content which was higher than 20% was that it was more beneficial for a small amount of oils and/or fats to permeate out from the cover for moxibustion and contact with the skin directly.

(14) In the examples, effective drug ingredients could be added without adding the drug powder. As compared with the ordinary medicinal moxa sticks (for example, thunder-fire miraculous moxa sticks and taiyi miraculous moxa sticks), the problem that drugs could only be added by mixing the drug powder was solved, and the effect of completely changing the route of adding drugs was achieved. There was no need to first grind the drugs into powder (or use a grinding machine to produce powder) and the drugs were soaked directly instead. As compared with the ordinary medicinal moxa sticks (for example, thunder-fire miraculous moxa sticks and taiyi miraculous moxa sticks), the problem that a grinding apparatus was needed was solved, and the effect of simplifying the preparation process was achieved. The problem that the drug powder might not be distributed evenly was solved, and the effect of the uniform distribution of the drug ingredients was achieved. The problem that the content of the drug powder might be too high was solved, and the effect of not increasing the powdery solid ingredients was achieved. At the time of application, a small amount of oils and/or fats permeated out from the cover for moxibustion (dry paper, cloth, etc.) and contacted with the skin directly, the effective drug ingredients could be absorbed through the skin directly under the function of moxibustion, thus combining the functions of moxibustion and the drugs to enhance the therapeutic effect. Meanwhile, a novel mode of administration was provided, i.e., the effective drug ingredients were dissolved using oils and/or fats, the oils and/or fats were brought into contact with the skin, and the effective drug ingredients were made to permeate through the skin more easily via the thermal effect of moxibustion. In other words, the moxa stick containing oils and/or fats provided a new route of administration.

CLINICAL EXPERIMENTAL CASES

EXAMPLE 1: Using the Present Disclosure to Improve the Preparation Method of Thunder-Fire Miraculous Moxa Stick Thunder-fire miraculous moxa stick was first seen in "Compendium of Materia Medica", Volume 6, Fire-moxibustion with miraculous moxa stick. The present disclosure was used to improve the preparation method as follows.

Step 1: Chinese medicines were soaked with olive oil. 9 gram of each of the following drugs were added to 500 gram of olive oil and soaked for 2 to 7 days to prepare the olive oil containing Chinese medicine ingredients: Amebiae Radix, Aquilariae Lignum Resinatum, Aucklandiae Radix, Olibanum, Artemisiae Scopariae Herba, Notopterygii Rhizoma et Radix, Zingiberis Rhizoma, Manis Squama.

Step 2: A pure moxa stick was prepared (it could be bought from the market directly). Generally, 60 gram of mugwort floss was taken and tiled on a cotton paper which was 50 cm in length, 20 cm in width, and had a soft, loose and tough texture, The cotton paper was rolled into a cylindrical shape with a diameter of about 3 cm, the tighter the better, and glue or paste was used to seal the opening to form the pure moxa stick.

Step 3: The pure moxa stick was soaked with the olive oil containing Chinese medicine ingredients. The pure moxa stick prepared in Step 2 was soaked with the olive oil prepared in Step 1 which contained Chinese medicines as effective ingredients for 5 to 10 hours, so that the soaking was sufficient. The pure moxa stick was taken out and dried in shade naturally, thus preparing the novel thunder-fire miraculous moxa stick, wherein the content of the oil and/or fat is more than 10%, more preferably 20% to 70%. About 10 moxa sticks could be soaked in 500 g of olive oil in Step 1.

Said olive oil might be substituted for tea oil, sunflower oil, olive oil, sesame oil, peanut oil, rapeseed oil, palm oil, soybean oil, tung oil, corn oil, castor oil, lard oil, badger oil, sheep oil, beef lard, refined oil, mixed oil, blend oil, and the like, and the following examples applied to this principle as well.

Said soaking might also be substituted by other contacting methods such as flushing, drip filling, spraying, fumigating, and the following examples applied to this principle as well.

Said Step 1 and Step 3 might be carried out at the same time, i.e., the moxa stick prepared in Step 2 were soaked with various Chinese medicines in the olive oil at the same time.

The application method was improved by the present disclosure. Step 1: The novel thunder-fire miraculous moxa stick was ignited by a fire source such as a butter lamp, a candle and a lighter, enabling it to burn for approximately 20 seconds. Step 2: The novel thunder-fire miraculous moxa stick was wrapped with 6-layer napkin or straw paper to extinguish the open fire. Step 3: The novel thunder-fire miraculous moxa stick was held in hand to give moxibustion, so as to treat diseases such as wind-cold-dampness arthralgia, flaccidity syndrome, stomachache, and diarrhoea.

Experimental Case 1: A patient, female, 28 years old. The bilateral wrist joints were swelling and painful for two weeks. A child was born via natural labour three weeks before, the patient did not take a good care of herself during the confinement in childbirth and used the cold water to wash clothes, resulting in unbearable swelling and pain of the bilateral wrist joints and being afraid of cold. The diet was as usual, the urine and stool had no abnormity, the pulse was deep and tense, and the tongue was pale with white coating. The diagnosis of western medicine: arthritis. Syndrome differentiation of traditional Chinese medicine: rheumatic arthralgia, cold-dampness type.

The novel thunder-fire miraculous moxa stick prepared in the present disclosure was used for the treatment. After the novel thunder-fire miraculous moxa stick was ignited, 6-layer straw paper was used to wrap it to extinguish the open fire, a small amount of olive oil would permeate out, then the novel thunder-fire miraculous moxa stick after being wrapped with straw paper was held in hand to give moxibustion directly. Moxibustion was first given from Baihui acupoint to Changqiang acupoint along Du Meridian, then was given from Baihui acupoint to Renzhong acupoint, and was given along Ren Meridian to perineum acupoint. During the process of giving moxibustion, the moxa stick stayed at each acupoint for 5 to 10 seconds, and finally moxibustion was focused on the swelling part of the wrist joints and moxibustion was given repeatedly until the affected area was hot and red and the pain was relieved significantly. The treatment was given daily, and the patient recovered after being treated for three times.

Experimental Case 2: A patient, male, 41 years old. A wound close to Chengshan acupoint at the lower end of the gastrocnemius muscle was painful for two years after being stitched. Two year ago, the lower end of the gastrocnemius muscle was scratched by glass in summer, the wound recovered well after seven stitches were given and only tiny scar remained. However, the pain persisted and aggravated on rainy days. The color of the affected area was slightly darker than that of the normal skin by the observation with naked eyes, the diet and the daily life was normal, the pulse was tense, and the tongue was light red with thin and white coating. Syndrome differentiation: After enquiring the patient, it was learned that the affected area was blown directly by the air conditioner immediately after the surgical suture, therefore, it was considered as the injury of the meridians and collaterals due to pathogenic cold.

The novel thunder-fire miraculous moxa stick prepared in the present disclosure was used for treatment. After the novel thunder-fire miraculous moxa stick was ignited, a simple cover for moxibustion made of 6-layer straw paper was used to wrap it to extinguish the open fire, a small amount of olive oil would permeate out, then the novel thunder-fire miraculous moxa stick after being wrapped with straw paper was held in hand to give moxibustion to the affected area directly. Moxibustion was given repeatedly until the affected area was hot and red and the color of the skin was close to the surrounding skin. The patient recovered after one treatment.

EXAMPLE 2: Using the Novel Medicinal Moxa Stick Prepared in the Present Disclosure to Treat Various Infections Preparation method: Step 1: A moxa stick was prepared (it could be bought from the market directly). Generally, 24 gram of mugwort floss was taken and tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form the moxa stick. According to the amount of the mugwort floss and the size of the cotton paper, moxa sticks of different sizes could be prepared.

Step 2: Chinese medicines and the moxa stick were flushed circularly with liquid sunflower seed oil. 10 moxa sticks, 10 gram of Phellodendri Chinensis Cortex, 10 gram of Coptidis Rhizoma, 10 gram of Sophorae Flavescentis Radix, 10 gram of Rhei Radix et Rhizoma, 10 gram of Dictamni Cortex, 10 gram of Salvia Chinensis, 10 gram of Violae Herba, 10 gram of Paridis Rhizoma, 10 gram of Alumen, 10 gram of Cnidii Fructus, and 5 gram of Borneolum Syntheticum were added to 2000 gram of sunflower seed oil, and flushed circularly for 2 to 7 days. "Flushed circularly" meant that a certain amount of liquid flew circularly within a closed loop device and the substance being flushed was set at a certain segment, like the water circulating constantly in a goldfish bowl.

Step 3: The moxa stick in Step 2 was taken out. The moxa stick in Step 2 was taken out and spin-dried until the content of sunflower oil was 20%, thus preparing the novel medicinal moxa stick.

Application Method

Step 1: The novel medicinal moxa stick was ignited by a fire source such as a butter lamp, a candle and a lighter, enabling it to burn for approximately 20 seconds.

Step 2: 6-layer napkin or straw paper was used to prepare a simple cover for moxibustion, with which the novel medicinal moxa stick was wrapped so that the open fire was extinguished.

Step 3: The novel medicinal moxa stick was held in hand to give moxibustion, so as to treat infections such as the infections of the wounds after surgery and dermatophytosis.

Experimental Case 3: A patient, female, 26 years old. Infections occurred repeatedly under the left armpit for two months after the sweat gland resection. Resection of the large sweat glands under bilateral armpits was performed two months ago due to bromhidrosis, after the surgery, the right side recovered well, the left side was infected repeatedly with unbearable pruritus, and a pale yellow liquid permeated out after squeezing. The urine was yellow, the stool was dry and was defecated once every two days, the pulse was slippery and rapid, and the tongue was red with thick yellow coating.

After the novel medicinal moxa stick prepared in the present disclosure was ignited, a simple cover for moxibustion made of 6-layer straw paper was used to wrap it to extinguish the open fire, and a small amount of sunflower seed oil would permeate out at once. Moxibustion was given to the affected area directly and repeatedly, and itching was immediately relieved at that moment. Moxibustion was given once per day, and the patient recovered after half a month.

The Chinese medicines might also not be added, the moxa stick containing oil and/or fat was prepared by flushing the moxa stick with sunflower seed oil and was used to perform moxibustion. In this way, the moxa stick was only lack of the pharmaceutical effects of the Chinese medicines while the therapeutic effect of moxibustion itself were not influenced, and it could treat the relevant diseases as well. Similarly, drug ingredients might not be added in all of the following examples, especially for some diseases which did not need extra drugs for adjuvant therapy. A redundant description would not be provided any more.

EXAMPLE 3: Preparing a Novel Medicinal Moxa Stick Used for Treating Phlegm Nodes Phlegm nodes referred to node-like phymas swelling subcutaneously, which were mostly formed by the flow and aggregation of damp phlegm. The phymas were different in numbers, neither red nor swelling, neither hard nor painful, and generally would not suppurate and ulcerate if the phymas were soft and smooth like a fruit kernel and might move when touching by hand. The phlegm nodes mostly appeared on neck, nape and lower jaw, and also appeared on limbs, shoulder and back. Most of the phlegm nodes appeared on the upper part of the body had wind-heat, and most of those appeared on the lower part of the body had damp-heat.

Preparation Method

Step 1: The Chinese medicines were soaked with ethanol. 500 gram of ethanol was taken, 10 gram of Pharbitidis Semen, 10 gram of Kansui Radix, 10 gram of White Mustard Seed, 10 gram of Pinelliae Rhizoma, 10 gram of Prunellae Spica, 10 gram of Arisaematis Rhizoma, 10 gram of Vaccariae Semen, 10 gram of Corydalis Rhizoma, 10 gram of Fritillariae Cirrhosae Bulbus, 10 gram of Concha Meretricis seu Cyclinae, 5 gram of borax, and 5 gram of Borneolum Syntheticum were added and soaked for 2 to 7 days to prepare the ethanol containing Chinese medicine ingredients.

Step 2: A pure moxa stick was prepared (it could be bought from the market directly). Generally, 24 gram of mugwort floss was taken and tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form the pure moxa stick. According to the amount of the mugwort floss and the size of the cotton paper, moxa sticks of different sizes could be prepared.

Step 3: The pure moxa stick was drip filled with the ethanol processed in Step 1. The pure moxa stick prepared in Step 2 was drip filled with the ethanol prepared in Step 1 which contained the Chinese medicine ingredients, enabling it to absorb the drug solution sufficiently till saturation. The pure moxa stick was taken out and dried in the air, thus preparing a dry medicinal moxa stick.

Step 4: The medicinal moxa stick processed in Step 3 was soaked with tea oil and prepared into the novel medicinal moxa stick. The medicinal moxa stick processed in Step 3 was soaked with tea oil for 5 to 10 hours, so that the soaking was sufficient. The medicinal moxa stick was taken out and dried in shade naturally until it contained 30% of oil and/or fat, thus preparing the novel medicinal moxa stick.

Among Step 1, Step 2 and Step 3, Step 2 might also be first carried out to prepare the moxa stick, then the moxa stick and the Chinese medicines were soaked in the ethanol at the same time, and Step 4 was carried out after drying. Or, the mugwort floss was first soaked with the ethanol containing the Chinese medicine ingredients in Step 2 and prepared into the moxa stick after drying, and Step 4 was carried out thereafter.

Application method: Step 1: The novel medicinal moxa stick was ignited by a fire source such as a butter lamp, a candle and a lighter, enabling it to burn for approximately 20 seconds. Step 2: A 6-layer dry napkin or straw paper was used to prepare a simple cover for moxibustion, with which the novel medicinal moxa stick was wrapped so that the open fire was extinguished. Step 3: The novel medicinal moxa stick was held in hand to give moxibustion, so as to treat scrofula, lymphadenectasis, lymphoma, etc.

Experimental Case 4: A patient, female, 53 years old. A phlegm node had grown close to Taichong acupoint on the dorsum of right foot for half a year. The color was same as the normal skin, and the phlegm node was about 5 mm higher than the skin and was spherical. There was a tight feeling, and it was painful sometimes. The patient had thick sputum in the mouth when she waked up in the morning. The pulse was deep and slippery, and the tongue was pale with white coating. Syndrome differentiation of traditional Chinese medicine: phlegm node.

After the novel medicinal moxa stick prepared in the present disclosure was ignited, a simple cover for moxibustion made of 6-layer straw paper was used to wrap it to extinguish the open fire, and a small amount of tea oil would permeate out at once. Moxibustion was given to the affected area directly and repeatedly, and the phlegm node became soft at once. Moxibustion was given once per day, and the patient recovered after being treated for 20 times in half a month.

EXAMPLE 4: Preparing a Novel Medicinal Moxa Stick Used for Treating Cough and Asthma Preparation Method Step 1: A pure moxa stick was prepared (it could be bought from the market directly). Generally, 24 gram of mugwort floss was taken and tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form the pure moxa stick. According to the amount of the mugwort floss and the size of the cotton paper, moxa sticks of different sizes could be prepared.

Step 2: The Chinese medicines and the pure moxa stick prepared in Step 1 were soaked in the mixed oil and/or fat of palm oil and sesame oil at the same time. 500 gram of palm oil and 50 gram of sesame oil were taken, 10 gram of Sanguisorbae Radix, 5 gram of Asari Radix et Rhizoma, 10 gram of Zingiberis Rhizoma, 10 gram of Fructus Schisandrae Chinensis, 10 gram of Pinelliae Rhizoma, 10 gram of Trichosanthis Fructus, 10 gram of apricot kernel, 10 gram of Perilla seed, 10 gram of Stemonae Radix, 10 gram of Eriobotryae Folium, 10 gram of Descurainiae Semen Lepidii Semen, 10 gram of Platycodonis Radix, 5 gram of Borneolum Syntheticum, and 10 moxa sticks were added and soaked for 2 to 7 days. The moxa stick was taken out and left for a while until the content of the mixed oil and/or fat accounted for approximately 60%, thus preparing the novel medicinal moxa stick containing the Chinese medicine ingredients. The Chinese medicine ingredients might not be added in this step, and the moxa stick was prepared by soaking the moxa stick only with the mixed oil and/or fat.

Application method: Step 1: The novel medicinal moxa stick was ignited by a fire source such as a butter lamp, a candle and a lighter, enabling it to burn for approximately 20 seconds. Step 2: A 6-layer dry napkin or straw paper was used to prepare a simple cover for moxibustion, with which the novel medicinal moxa stick was wrapped so that the open fire was extinguished.

Step 3: The novel medicinal moxa stick was held in hand to give moxibustion.

Experimental Case 5:

A patient, male, 11 years old, suffered from asthma for three years. The disease was aggravated in winter or in cold weather, there was moist rale in lungs, large amount of sputum was coughed out when waking up in the morning. The patient was afraid of cold, and had a pale face, poor appetite, cold limbs, a tense pulse, and a moistened tongue with much saliva and white coating. Syndrome differentiation of traditional Chinese medicine: syndrome of cold fluid-retention.

Treatment: The above-mentioned novel medicinal moxa stick used for treating cough and asthma was ignited, enabling it to burn for 10 to 20 seconds. A 6-layer napkin was used to prepared a simple cover for moxibustion, with which the burning end of the novel medicinal moxa stick was wrapped and the fire was extinguished. Moxibustion was given to the Baihui acupoint, Yuzhen acupoint, Fengchi acupoint, Fengfu acupoint, Dazhui acupoint, Feiyu acupoint, Tiantu acupoint, Jianjing acupoint of the patient in turn by holding the novel medicinal moxa stick in hand. It took approximately 1 minute for each acupoint. The condition was relieved at once, once-a-day treatment was persisted thereafter, various symptoms were gradually alleviated, and the patient was the same as the normal people after 10 days.

EXAMPLE 5: A Novel Medicinal Moxa Stick Used for Treating Ankylosing Spondylitis Ankylosing spondylitis was equivalent to "Wanbi (also referred to as lame impediment)" described in the ancient books of Chinese medicine, and was a chronic persistent disease in medicine characterized by the inflammations and ossifications of the joints and ligaments of waist, neck and thoracic spine as well as the sacroiliac joints. The hip joints were often affected, and other periphery joints might also develop inflammations. This disease had an insidious onset with slow progress and mild systemic symptoms. Low back pain and morning stiffness often appeared in the early stage and were alleviated after activity, and they might be accompanied by symptoms such as low fever, fatigue, loss of appetite and weight loss. In the beginning, the pain was intermittent and developed to persistent after several months or several years, afterwards, the inflammatory pain disappeared, the spine was partially or completely rigid from the bottom to the top, and kyphosis of spine appeared.

Preparation Method

Step 1: The Chinese medicines were soaked with sesame oil. 1000 gram of sesame oil was taken and the following Chinese medicines were added and soaked for 2 to 7 days to prepare the sesame oil containing the Chinese medicine ingredients: 10 gram of Psoraleae Fructus, 15 gram of Radix Rehmanniae Preparata, 10 gram of Radix Dipsaci, 12 gram of Epimedii Folium, 6 gram of mix-fried pangolin scales, 10 gram of Saposhnikoviae Radix, 10 gram of processed aconite, 15 gram of Drynariae Rhizoma, 10 gram of Cinnamomi Ramulus, 10 gram of Paeoniae Radix Rubra and 10 gram of Paeoniae Radix Alba, 15 gram of Anemarrhenae Rhizoma, 10 gram of Notopterygii Rhizoma et Radix and 10 gram of Angelicae Pubescentis Radix, 10 gram of Pine Nodular Branch, 10 gram of Eupolyphaga Seu Steleophaga, 6 gram of Ephedrae Herba, 10 gram of Atractylodis Rhizoma, 12 gram of Clematidis Radix et Rhizoma, 20 gram of Lycopodii Herba, 15 gram of Achyranthis Bidentatae Radix, 20 gram of Trberculate Speranskia Herb, 15 gram of Herba Aristolochiae Mollissimae, 9 gram of native copper, 10 gram of Angelicae Sinensis Radix, 10 gram of Carthami Flos, and 3 gram of Borneolum Syntheticum.

Step 2: The mugwort floss was sprayed with the sesame oil prepared in Step 1. Generally, 250 gram of mugwort floss was taken and sprayed with the sesame oil prepared in Step 1, enabling the mugwort floss to absorb sufficiently.

Step 3: The novel medicinal moxa stick was prepared directly using the mugwort floss processed in Step 2. The mugwort floss in Step 2 was taken out, after squeezing out part of the sesame oil, the mugwort floss was divided into ten equal parts, each part was twisted into strips, and the novel medicinal moxa stick was directly prepared by wrapping the strips with cotton paper.

Application method: Step 1: The novel medicinal moxa stick was ignited by a fire source such as a butter lamp, a candle and a lighter, enabling it to burn for approximately 20 seconds. Step 2: A 6-layer dry napkin or straw paper was used to prepare a simple cover for moxibustion, with which the novel medicinal moxa stick was wrapped so that the open fire was extinguished.

Step 3: The novel medicinal moxa stick was held in hand to give moxibustion.

Experimental Case 6:

A patient, male, 40 years old, suffered from the pain in sacroiliac joints for five years and the pain was aggravated for a month. The patient was a retired basketball player, when he was young, he took a cold shower each time after training when sweating profusely. His waist and hip began to ache since five years ago and the symptom was aggravated on rainy days. The diagnosis of western medicine: ankylosing spondylitis. The symptom was aggravated a month ago as a result of catching a chill accidentally. Now the pain in the lumbosacral portion was unbearable, the activity was limited, the stool was thin and loose, the pulse was deep, thin and tense, and the tongue was dark with less coating. Syndrome differentiation of traditional Chinese medicine: Wanbi.

Treatment: The above-mentioned novel medicinal moxa stick used for treating ankylosing spondylitis was ignited, enabling it to burn for 10 to 20 seconds. A 6-layer napkin was used to prepare a simple cover for moxibustion, with which the burning end of the novel medicinal moxa stick was wrapped and the fire was extinguished. Moxibustion was given to the Du Meridian, Ren Meridian, kidney meridian, and liver meridian of the patient in turn by holding the novel medicinal moxa stick in hand, and moxibustion was focused on acupoints such as Guanyuan, Qihai, Zhongji, Huiyin, Baliao, Shenyu, Mingmen and Yaoyangguan. The condition was relieved at once, once-a-day treatment was persisted thereafter and the Chinese medicines were orally administered together, various symptoms were gradually alleviated, and the mobility of the patients was greatly improved after 30 days.

EXAMPLE 6: A Novel Medicinal Moxa Stick Used for Treating Stomachache and Diarrhea Preparation Method Step 1: The Chinese medicines were soaked with sesame oil. 1000 gram of sesame oil was taken, 10 gram of Euodiae Fructus, 10 gram of Atractylodis Macrocephalae Rhizoma, 10 gram of Poria, 10 gram of Mume Fructus, 10 gram of Codonopsis Radix, 10 gram of Angelicae Sinensis Radix, 10 gram of Coptidis Rhizoma, 10 gram of Phellodendri Chinensis Cortex, 10 gram of Asari Radix et Rhizoma, 10 gram of Zanthoxyli Pericarpium, 10 gram of Zingiberis Rhizoma, 10 gram of Cinnamomi Ramulus, 10 gram of Aconiti Lateralis Radix Praeparaia, 10 gram of Chebulae Fructus, 10 gram of Myristicae Semen and 10 gram of Fructus Schisandrae Chinensis were added and soaked for 2 to 7 days, thus preparing the sesame oil containing the Chinese medicine ingredients. This step might also be omitted, i.e., no Chinese medicine ingredient was added in the sesame oil.

Step 2: The mugwort floss was soaked with the sesame oil prepared in Step 1. 250 gram of mugwort floss was soaked with the sesame oil prepared in Step 1 for 5 to 10 hours and taken out.

Step 3: The cotton papers were sprayed with the sesame oil prepared in Step 1. 10 pieces of cotton paper (250 mm*200 mm) were taken and sprayed with the sesame oil prepared in Step 1, enabling them to be sprayed sufficiently and dried in shade.

Step 4: The novel medicinal moxa stick was prepared. The mugwort floss prepared in Step 2 was twisted into strips, then the strips were wrapped with the cotton paper prepared in Step 3 into the novel medicinal moxa stick containing 50% of oil and/or fat.

Step 2 and Step 3 might be carried out at the same time.

Application method: Step 1: The novel medicinal moxa stick was ignited by a fire source such as a butter lamp, a candle and a lighter, enabling it to burn for approximately 20 seconds. Step 2: A 6-layer napkin or straw paper was used to prepare a simple cover for moxibustion, with which the novel medicinal moxa stick was wrapped so that the open fire was extinguished.

Step 3: The novel moxa stick was held in hand to perform moxibustion.

Experimental Case 7:

A patient, male, 35 years old, suffered from stomachache and diarrhea for three years. The patient suffered from acute enteritis as a result of overeating watermelon in summer three years ago and was cured with anti-inflammatory drugs. After the beginning of autumn, the disease recurred due to the careless diet. The patient suffered from stomachache and diarrhea, defecated five times or more every day, the stool was thin and loose. The symptoms were relieved and aggravated now and then, and the disease was persistent. The body weight of the patient had been reduced from 65 kg to 47.5 kg in the past three years. Now the patient felt weak in the legs, had difficulty to stand, felt palpitation and short breath, and had water-like stool. The patient was diagnosed with hypokalemia by the assay of western medicine, and had bitter taste, a thready and rapid pulse, and a slim tongue with tiny cracks and less coating. Syndrome differentiation of traditional Chinese medicine: syndrome of deficiency of spleen-yang and kidney-yang.

Treatment: The above-mentioned novel medicinal moxa stick used for treating stomach ache and diarrhea was ignited and burned for 10 to 20 seconds. A 6-layer napkin was used to prepare a simple cover for moxibustion, with which the burning end of the novel medicinal moxa stick was wrapped and the fire was extinguished. Moxibustion was repeatedly given to acupoints such as Zhongwan, Guanyuan, Qihai, Zhongji, Huiyin and Zusanli. The condition was relieved at once, once-a-day treatment was persisted thereafter and Mume Fructus Pill was orally administered with the treatment, the condition was gradually improved, and the patient had formed stool twice a day after 7 days.

EXAMPLE 7: A Novel Medicinal Moxa Stick Prepared by Antibiotics

Preparation Method

Step 1: The antibiotics were soaked with tea oil. 500 gram of tea oil was taken, 5 vials of penicillin, 10 tablets of metronidazole, 10 tablets of terramycin were added and soaked for 2 to 7 days, thus preparing the sesame oil containing drug ingredients.

Step 2: A pure moxa stick was prepared (it could be bought from the market directly). Generally, 24 gram of mugwort floss was taken and tiled on a cotton paper which was 26 cm in length, 20 cm in width, and had a soft, loose and tough texture. The cotton paper was rolled into a cylindrical shape with a diameter of about 1.5 cm, the tighter the better, and glue or paste was used to seal the opening to form the pure moxa stick. According to the amount of the mugwort floss and the size of the cotton paper, moxa sticks of different sizes could be prepared.

Step 3: The pure moxa stick was soaked with the tea oil processed in Step 1. The pure moxa stick prepared in Step 2 was soaked with the tea oil prepared in Step 1 which contained drug ingredients for 5 to 10 hours, so that the soaking was sufficient. The pure moxa stick was taken out and dried in shade naturally until it contained 40% of tea oil, thus a novel medicinal moxa stick was prepared. About 10 moxa sticks could be soaked in 500 gram of the tea oil in Step 1.

Application method: Step 1: The novel medicinal moxa stick was ignited by a fire source such as a butter lamp, a candle and a lighter, enabling it to burn for approximately 20 seconds. Step 2: A 6-layer napkin or straw paper was used to prepare a simple cover for moxibustion, with which the novel medicinal moxa stick was wrapped so that the open fire was extinguished.

Step 3: The novel moxa stick was held in hand to give moxibustion, so as to treat the wound infections after surgery.

Experimental Case 8:

A patient, female, 33 years old. After the suture of the wound of caesarean, the wound was repeatedly infected with suppuration for seven years. The patient gave birth to a child seven years ago by caesarean. The wound was repeatedly infected after the suture, and was especially severe in summer. The itching was unbearable, and there was pus flowing out when squeezing.

Treatment: The above-mentioned novel medicinal moxa stick prepared by antibiotics was ignited and burned for 10 to 20 seconds. A 6-layer napkin was used to prepare a simple cover for moxibustion, with which the burning end of the novel medicinal moxa stick was wrapped and the fire was extinguished. Moxibustion was given to the affected area repeatedly. The condition was relieved at once, once-a-day treatment was persisted thereafter, and the patient recovered after 10 days.

The followings could be seen from the above-mentioned examples. (1) The preferred content of the oil and/or fat added in the moxa stick. The higher the oil content, the better the smoke could be reduced and the burning intensity could be controlled, however, it was easy to cause oil dripping at the time of application if the oil content was too high. Therefore, the advantage of a content which was lower than 70% (especially 60%) was that frequent oil dripping at the time of application would not be caused by the excessive high content of the oils and/or fats, and the frequent oil dripping would influence the experience of the patients and would be more easily to cause scald. The advantages of a content which was higher than 20% (especially 30%) were that the smoke was reduced, the burning intensity was controlled, and a proper temperature of moxibustion was selected. Meanwhile, it was more beneficial for a small amount of oils and/or fats to permeate out of the cladding(s) to contact with the skin directly and enhance the therapeutic effect of moxibustion. After multiple tests, the content of oils and/or fats was preferably 20% to 70%, and 30% to 60% was the most preferred value, which was able to achieve the above-mentioned optimal effects. (2) The drugs were brought into contact with the oils and/or fats, so as to enable the effective ingredients thereof to be partially or completely dissolved in the oils and/or fats. The effective ingredients and the oils and/or fats complemented each other, and enhanced the therapeutic effects mutually, not just achieving the effect of simple superposition. At the time of application, a small amount of oils and/or fats permeated out from the wrapper (dry paper, cloth, etc.) and contacted with the skin directly, the effective drug ingredients could be absorbed through the skin directly under the function of moxibustion, thus combining the functions of moxibustion and the drugs to enhance the therapeutic effect. Meanwhile, since the moxa stick needed to be ignited, from the traditional viewpoints, drugs could not be added into the moxa stick after being dissolved (solvents such as water might influence the burning of the moxa stick, and organic solvents such as alcohol and petrol burned much too fiercely, which was easy to cause danger). The present disclosure also overcame the traditional prejudice and improved the method of adding drugs in the moxa stick to enhance the pharmaceutical effects. (3) One or more kinds of drugs having therapeutic effect for scald could be selected, the advantage of doing so was that the oils and/or fats had therapeutic effect for scald after absorbing the ingredients of the drugs for scald, then other drugs which were needed to achieve certain therapeutic aims were selected. According to clinical practical experience, this would not cause damage to the skin even if the temperature was slightly higher. Thus, from another viewpoint, this made it possible to contact with the skin when only several layers of dry paper separated therebetween. Since the moxa stick could be very close to the skin at the time of application, the therapeutic effect of the moxibustion was good. Drugs having therapeutic effect for scald included Catechu, Scutellariae Radix, Amebiae Radix, Phellodendri Chinensis Cortex, Bomeolum Syntheticum, Sanguisorbae Radix, Rhei Radix et Rhizoma, Polygoni Cuspidati Rhizoma et Radix, Coptidis Rhizoma, Ampelopsis Radix, Sepiae Endoconcha, Calamina, Myrrha, Gardeniae Fructus, Sophorae Flavescentis Radix, gypsum, dried alum, Indigo Naturalis, dried rehmannia, Carthami Flos, Angelicae Sinensis Radix, Radix Ophiopogonis, Bletillae Rhizoma, Draconis Sanguis, Sanguisorbae Radix, Folium Hibisci Mutabilis, Flos Hibisci Mutabilis, etc. If oils and/or fats such as tea oil, sea buckthorn seed oil, tung oil, badger oil and lard oil that had therapeutic effects for scald themself were used, the above-mentioned drugs having therapeutic effects for scald might also not be added additionally. (4) The moxa stick was brought into contact (for example, soaking and the like) with oils and/or fats and contained 10% or more of the oils and/or fats after being prepared, thus enabling the moxa stick to remain in an incompletely dry state so as to be capable of reducing the smoke produced in the burning of the moxa stick. Also, by wrapping the ignited moxa stick with dry paper or cloth, the open fire of the moxa stick could be extinguished and the temperature of the moxa stick was ensured at an acceptable temperature for human body, so that moxibustion could be achieved when the above-mentioned dry paper separated therebetween. If the moxa stick was not soaked with oils and/or fats, then the moxa stick burned fiercely and could not stay too close to the skin or need to be separated by other spacers that influenced the convenience of use (for example, wet paper, ginger slice, or the like was placed on the skin).

The above examples are merely limited enumeration, and do not limit the preparation methods and the structures of the moxa sticks. It can be understood by those skilled in the art that the different raw materials and different methods used in the various examples can be used interchangeably, as long as it is ensured that the moxa sticks eventually contain the oils and/or fats and/or the drugs.

What is claimed is:

1. A moxibustion material containing oil and/or fat, comprising a processed product of wormwood and an externally added oil and/or externally added fat; the processed product of wormwood absorbs said oil and/or fat via contact; the weight of said oil and/or fat accounts for 20% to 70% of the total weight of the moxibustion material containing oil and/or fat, said oil and/or fat includes a vegetable oil and/or fat, an animal oil and/or fat, a processed product of vegetable oil and/or fat or a processed product of animal oil and/or fat, and wherein the moxibustion material containing oil and/or fat is a moxa stick prepared by wrapping the processed product of wormwood partially or completely with a wrapper, or a moxa stick prepared by the processed product of wormwood via a viscous substance or via extrusion by an external force.

2. The moxibustion material containing oil and/or fat according to claim 1, wherein said oil and/or fat includes one or more of tea oil, sunflower oil, Litsea Cubeba oil, sea buckthorn seed oil, olive oil, sesame oil, peanut oil, rapeseed oil, palm oil, soybean oil, tung oil, corn oil, castor oil, lard oil, badger oil, sheep oil, beef lard, refined oil, mixed oil, or blend oil, or the above-mentioned oil and/or fat is a reprocessed product of one or more of the above-mentioned oils.

3. The moxibustion material containing oil and/or fat according to claim 1, wherein said processed product of wormwood is mugwort floss, Blumea balsamifera powder, stockpiled Artemisiae Argyi Folium, a moxa stick, or a processed product mixed with other materials and a wormwood ingredient.

4. The moxibustion material containing oil and/or fat according to claim 1, wherein said contact includes one or more of soaking, flushing, drip filling, fumigating, spraying, or contacting dispersedly after solidification.

5. The moxibustion material containing oil and/or fat according to claim 1, wherein in an environment with an ambient temperature, the moxibustion material containing oil and/or fat is in an incompletely dry state.

6. The moxibustion material containing oil and/or fat according to claim 1, wherein said wrapper is paper, or cloth, or other processed products of plant fiber.

* * * * *